United States Patent [19]

Bower

[11] Patent Number: 5,434,072
[45] Date of Patent: Jul. 18, 1995

[54] METHOD FOR PREPARING AN AQUEOUS SOLUTION ENRICHED IN BOTH EG-III & XYLANASE USING A LOW MOLECULAR WEIGHT ALCOHOL AND AN ORGANIC SALT

[75] Inventor: Benjamin S. Bower, San Francisco, Calif.

[73] Assignee: Genencor International, Inc., San Francisco, Calif.

[21] Appl. No.: 228,988

[22] Filed: Apr. 18, 1994

Related U.S. Application Data

[62] Division of Ser. No. 862,641, Apr. 3, 1992, Pat. No. 5,320,960.

[51] Int. Cl.$^6$ .......................... C12N 9/24; C12N 9/42
[52] U.S. Cl. .................... 435/200; 435/209; 435/814; 435/816
[58] Field of Search ............... 435/183, 209, 200, 201, 435/205, 814, 816

[56] References Cited

U.S. PATENT DOCUMENTS

| | | | |
|---|---|---|---|
| 4,275,163 | 6/1981 | Gallo | 435/209 |
| 4,435,307 | 3/1984 | Barbesgaard et al. | 252/174.12 |
| 4,472,504 | 9/1984 | Gallo | 435/209 |
| 4,479,881 | 10/1984 | Tai | 252/8.8 |
| 4,487,831 | 12/1984 | Day et al. | 435/99 |
| 4,648,979 | 3/1987 | Parslow et al. | 252/8.8 |
| 4,661,289 | 4/1987 | Parslow et al. | 252/547 |
| 4,725,544 | 2/1988 | Tan et al. | 435/200 |
| 4,738,682 | 4/1988 | Boegh et al. | 8/401 |
| 4,746,517 | 5/1988 | Ducroo | 426/12 |
| 4,762,788 | 8/1988 | Warzywoda et al. | 435/209 |
| 4,797,361 | 1/1989 | Montenecourt | 435/198 |
| 4,822,516 | 4/1989 | Suzuki et al. | 252/174.12 |
| 4,832,864 | 5/1989 | Olson | 252/174.12 |
| 4,894,338 | 1/1990 | Knowles et al. | 435/172.3 |
| 4,912,056 | 3/1990 | Olson | 435/263 |
| 4,945,053 | 7/1990 | Ito et al. | 435/209 |
| 4,952,505 | 8/1990 | Cho | 435/209 |
| 4,954,447 | 9/1990 | Nevins et al. | 435/200 |
| 4,978,470 | 12/1990 | Suzuki et al. | 252/174.12 |
| 5,006,126 | 4/1991 | Olson et al. | 8/401 |
| 5,045,464 | 9/1991 | Ito et al. | 435/209 |
| 5,116,746 | 5/1992 | Bernier et al. | 435/172.3 |
| 5,120,463 | 6/1992 | Bjork et al. | 252/174.12 |
| 5,183,753 | 2/1993 | Wizani et al. | 435/201 |

OTHER PUBLICATIONS

S. Aho, "Structural and functional analysis of Trichoderma reesei endoglucanase I expressed in yeast Saccharomyces cerevisiae", FEBS Letters, vol. 291, pp. 45-49 (1991).

Berg et al., "Enzyme-Gold Affinity Labelling of Cellulose", Journal of Electron Microsc. Tech., vol. 8, pp. 371-379, (1988) [Abstract].

Bhat et al., Carbohydrate Research, vol. 190, pp. 279-297 (1989).

Brown et al., "Microbial Enzymes and Lignocellulose Utilization," Genetic Control of Environmental Pollutants, Omen Editor, Plenum Publishing Corp., pp. 239-265 (1984).

(List continued on next page.)

Primary Examiner—David M. Naff
Assistant Examiner—Mike Meller
Attorney, Agent, or Firm—Margaret A. Horn

[57] ABSTRACT

A method for preparing an aqueous solution enriched in xylanase only, EG III only and both EG III and xylanase from an aqueous mixture containing cellulase proteins, xylanase and EG III is disclosed. The methods involve adding an amount of a low molecular weight alcohol and an organic salt to an aqueous mixture containing cellulase proteins under conditions wherein substantially all of the cellulase proteins other than EG III and xylanase are precipitated out of the aqueous mixture. The methods can then involve adding an inorganic salt to the supernate produced in the previous step so as to form a second precipitate and a second supernate and then finally collecting either the second precipitate from the second supernate to obtain a precipitate enriched in xylanase or the second supernate from the second precipitate to obtain a supernate enriched in EG III.

8 Claims, 10 Drawing Sheets

OTHER PUBLICATIONS

Chen et al., "Nucleotide Sequence and Deduced Primary Structure of Cellobiohydrolase II from *Trichoderma reesei*", *Biotechnology*, vol. 5, pp. 274–278 (1987).

Corrick et al., *Gene* vol. 53, pp. 63–71 (1987).

Coughlan et al., "Comparative Biochemistry of Fungal and Bacterial Cellulolytic Enzyme Systems", *Biochemistry and Genetics of Cellulose Degradation*, Aubert et al., Editors, pp. 11–30 (1988).

Hakanssan, Dissertation, Faculty of Science, Uppsala University, pp. 6–23 (1981).

Hakansson et al., *Biochimica et Biophysica Acta* vol. 524, pp. 385–392 (1978).

Harkki et al., "Genetic engineering of Trichoderma to produce strains with novel cellulase profiles", *Enzyme Microb. Technol.*, vol. 13, pp. 227–233 (1991).

Hayashida et al., "Cellulases of *Humicola insolens* and *Humicola grisea*", *Methods in Enzymology*, vol. 160, pp. 323–332 (1988).

Hayashida et al., "Production and Purification of Thermostable Cellulases from *Humicola insolens* YH-8", *Agri. Biol. Chem.*, vol. 44(8), pp. 1721–1728 (1980).

Hayashida et al., "The Role of Carbohydrate Moiety on Thermostability of Cellulases from *Humicola insolens* YH-8", *Agri. Biol. Chem.*, vol. 44(3) pp. 481–487 (1980).

*International Textile Bulletin, Dyeing/Printing/Finishing*, 2nd Quarter, pp. 5–8 (1990).

JTN, "Weight Loss Treatment to Soften the Touch of Cotton Fabric", p. 64 (Dec. 1988).

Kenkyushitsu et al., "The Improvement of Cellulose Fibers by Means of Cellulase".

Knowles et al., "The Use of Gene Technology in the Development of Novel Cellulolytic Organisms—*Trichoderma reesei* Cellulase and Cellulobiohydrolase Gene Cloning and Expression; a Review", *Recent Adv. Biotechnol. Appl. Biol.*, pp. 139–142 (1988) [Abstract].

Knowles et al., "The use of gene technology to investigate fungal cellulolytic enzymes *Trichoderma reesei* cellulase complex gene cloning and expression in *Saccharomyces cerevisiae*", *FEMS Symp.* 43, pp. 153–169 (1988) [Abstract].

Kubicek-Pranz et al., "Transformation of *Trichoderma reesei* with cellobiohydrolase II gene as a means for obtaining strains with increased cellulase production and specific activity", *Journal of Biotechnology*, vol. 20, pp. 83–94 (1991).

Kubicek-Pranz et al., "Characterization of Commercial *Trichoderma-reesei* Cellulase Preparations by Denaturing Electrophoresis SDS-PAGE and Immunostaining Using Monoclonal Antibodies", *Biotechnol. Appl. Biochem.*, vol. 14, pp. 317–323 (1991) [Abstract].

Luderer et al., "A Re-appraisal of Multiplicity of Endoglucanase I from *Trichoderma reesei* Using Monoclonal Antibodies and Plasma Desorption Mass Spectrometry", *Biochim. Biophys. Acta*, vol. 1076, pp. 427–434 (1991) [Abstract].

Miller et al., "Direct and Indirect Gene Replacements in *Aspergillus nidulans*", *Mol. and Cell. Biol.*, vol. 5(7), pp. 1714–1721 (1985).

Murphy-Holland et al., "Secretion activity and stability of deglycosylated cellulase of *Trichoderma reesei* gene cloning", *Abstr. Annu. Meet. Am. Soc. Microbiol.*, 85 Meet., 193 (1985) [Abstract].

Ohishi et al., "Reformation of Cotton Fabric by Cellulase;" pp. 1–12.

Penttilla et al., "Homology between cellulase genes of *Trichoderma reesei*: complete nucleotide sequence of the endoglucanase I gene", *Gene*, vol. 45, pp. 253–263 (1986).

Penttilä et al., "Expression of Two *Trichoderma reesei* Endoglucanases in the Yeast *Saccharomyces cerevisiae*", *Yeast*, vol. 3, pp. 175–185 (1987).

Reinikainen et al., "How Do *Trichoderma Reesei* cellobiohydrolase bind to and degrade cellulose", *Abstr. Pap. Am. Chem. Soc.*, 202 Meet. Pt. 1 (1991) [Abstract].

Saloheimo et al., "EGIII a new endoglucanase from *Trichoderma reesei*:the characterization of both gene and enzyme", *Gene*, vol. 63, pp. 11–22 (1988).

Sambrook et al., *Molecular Cloning A Laboratory Manual*, 2nd Ed., Cold Spring Harbor Laboratory Press, pp. 1.53–1.73 (1989).

Schulein, "Cellulases of *Trichoderma reesei*", *Methods in Enzymology*, vol. 160, pp. 234–242 (1988).

Sheir-Neiss et al., "Characterization of the Secreted Celluloses of *Trichoderma reesei* Wild Type and Mutants During Controlled Permentations", *Appl. Microbiol. Biotechnol.*, vol. 20, pp. 46–53 (1984).

(List continued on next page.)

OTHER PUBLICATIONS

Shoemaker et al., "Molecular Cloning of Exo-cellobiohydrolase I Derived from *Trichoderma reesei* Strain L27", *Biotechnology*, vol. I, pp. 691 (1983).

Shoemaker et al., "Characterization and Properties of Cellulases Purified from *Trichoderma reesei* Strain L27", *Biotechnology*, pp. 687–690 (1983).

Smith et al., *Curr. Genetics*, vol. 19, pp. 27–33 (1991).

Teeri, "The Cellulolytic Enzyme System of Trichoderma reesei," *Publications* 38, pp. 13, 17–20 of 1–52+ Appendices (1987).

Teeri et al., "Engineering *Trichoderma* and its cellulases *Trichoderma reesei* cellulase and cellobiohydrolase gene cloning and expression: potential strain and improvement and enzyme engineering" *Trichoderma reesei Cellulases*, pp. 156–167 (1990) [abstract].

Ulker et al., "Characterization of an Unglycosylated Low Molecular Weight 1,4-B-glucan-glucanohydrolase of *Trichoderma reesei*", *FEMS Microbiology Letters*, vol. 69, pp. 215–219 (1990).

Uusitalo et al., "Enzyme Production by recombinant *Trichoderma reesei* strains" *Journal of Biotechnology*, vol. 17, pp. 35–49 (1991).

Van Arsdell *Bio/Technology* vol. 5, pp. 60–64 (1987).

Voragen et al., "Cellulase of a Mutant Strain of *Trichoderma viride QM 9414*", *Methods in Enzymology*, vol. 160, pp. 243–251 (1988).

Wilson *Nucl. Acids Res.* vol. 16, pp. 2339 (1988).

Wood "Properties of Cellulolytic Enzyme Systems", *Biochem. Soc. Trans.*, vol. 13, pp. 407–410 (1985).

Wood et al., "Aerobic and Anaerobic Fungal Cellulases, With Special Reference to Their Mode of Attack on Crystalline Cellulose", *Biochemistry and Genetics of Cellulose Degradation*, pp. 31–52 (1988).

Wood et al., "Methods for Measuring Cellulase Activities", *Methods in Enzymology*, vol. 160, pp. 87–112 (1988).

Wood et al., "The Mechanism of Fungal Cellulose Action", *Biochem J.*, vol. 260, pp. 37–43 (1989).

Yamagishi, "Reforming of Cellulosic Fiber With Cellulose", *The Shizuoka Prefectural Hamamatsu Textile Industrial Research Institute Report* vol. 24, pp. 54–61 (1986).

Englard, S. and Seifter, S., "Precipitation Techniques", Methods in Enzymology, vol. 182, (1990) pp. 285–300.

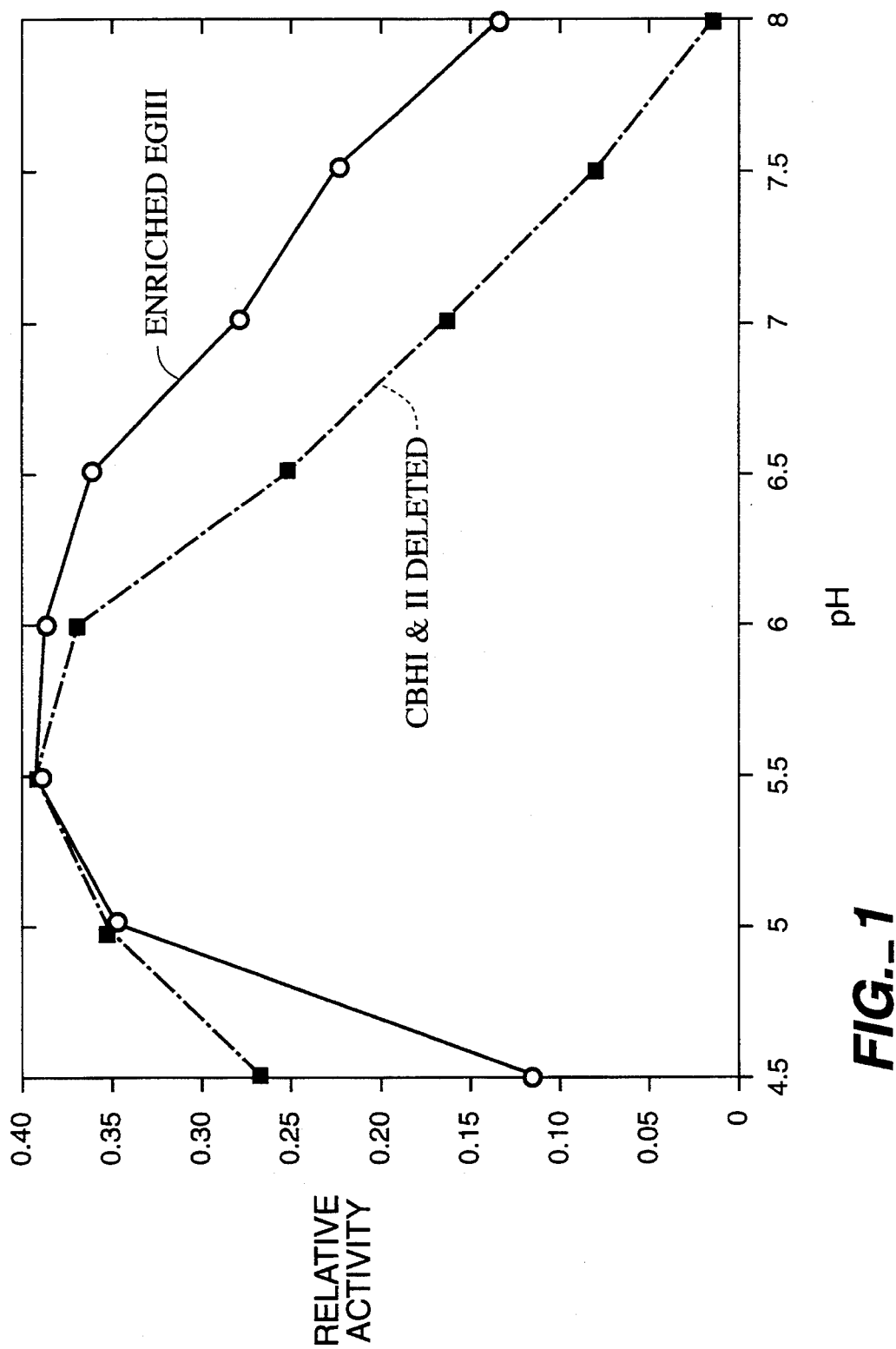
FIG._1

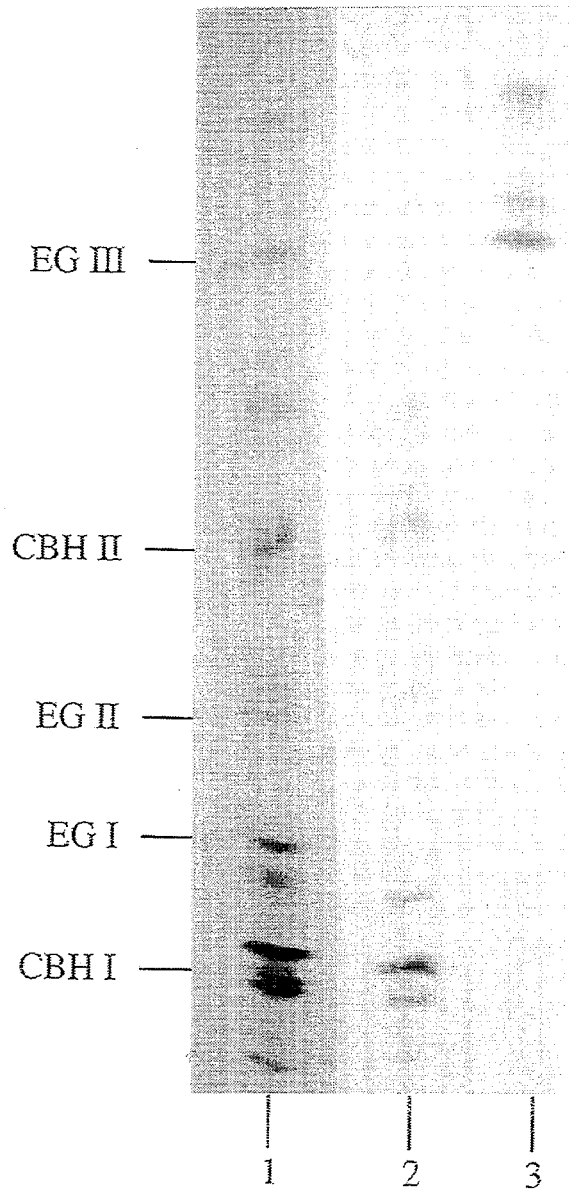
FIG._2

1) IWLGKYGDGPIGSSQGXVNVGGQ
2) PTTASWSYSGSNIRANVAYDLFTAAN
FIG._3
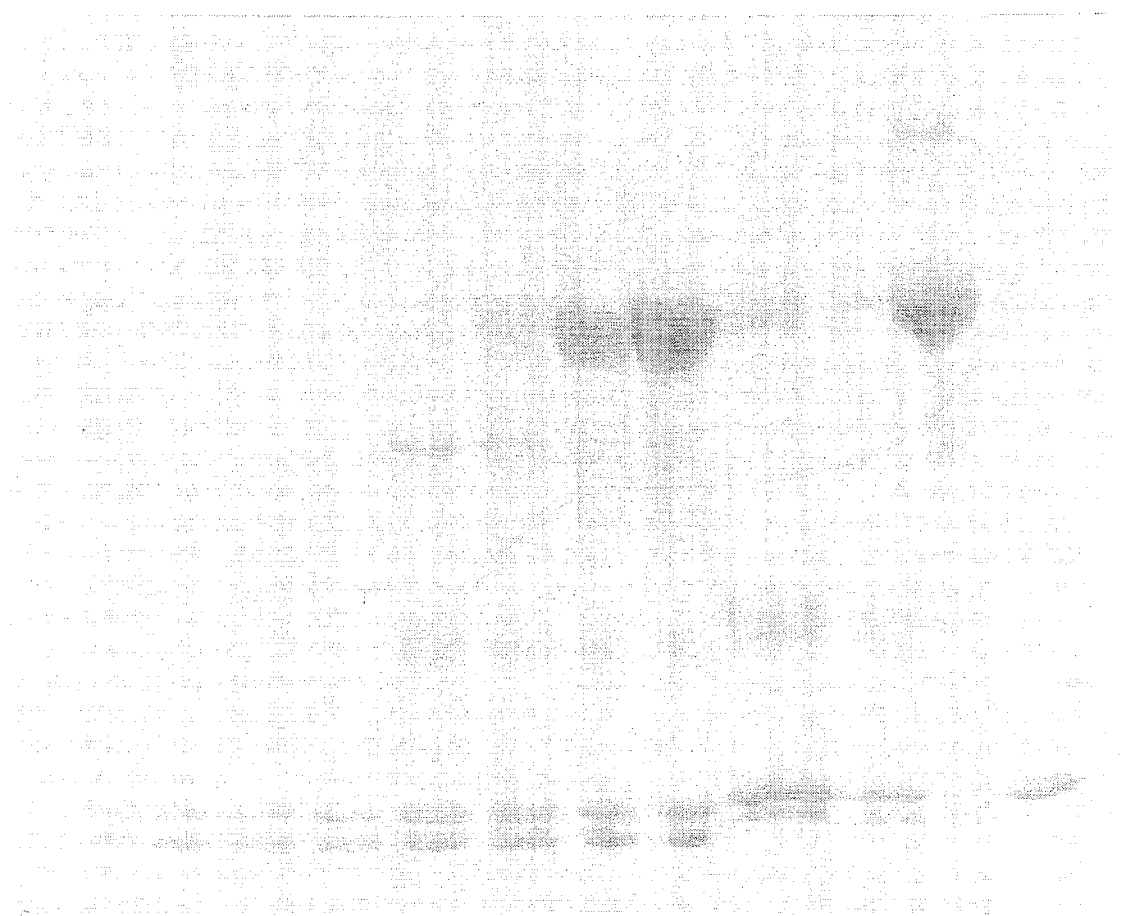
FIG._4

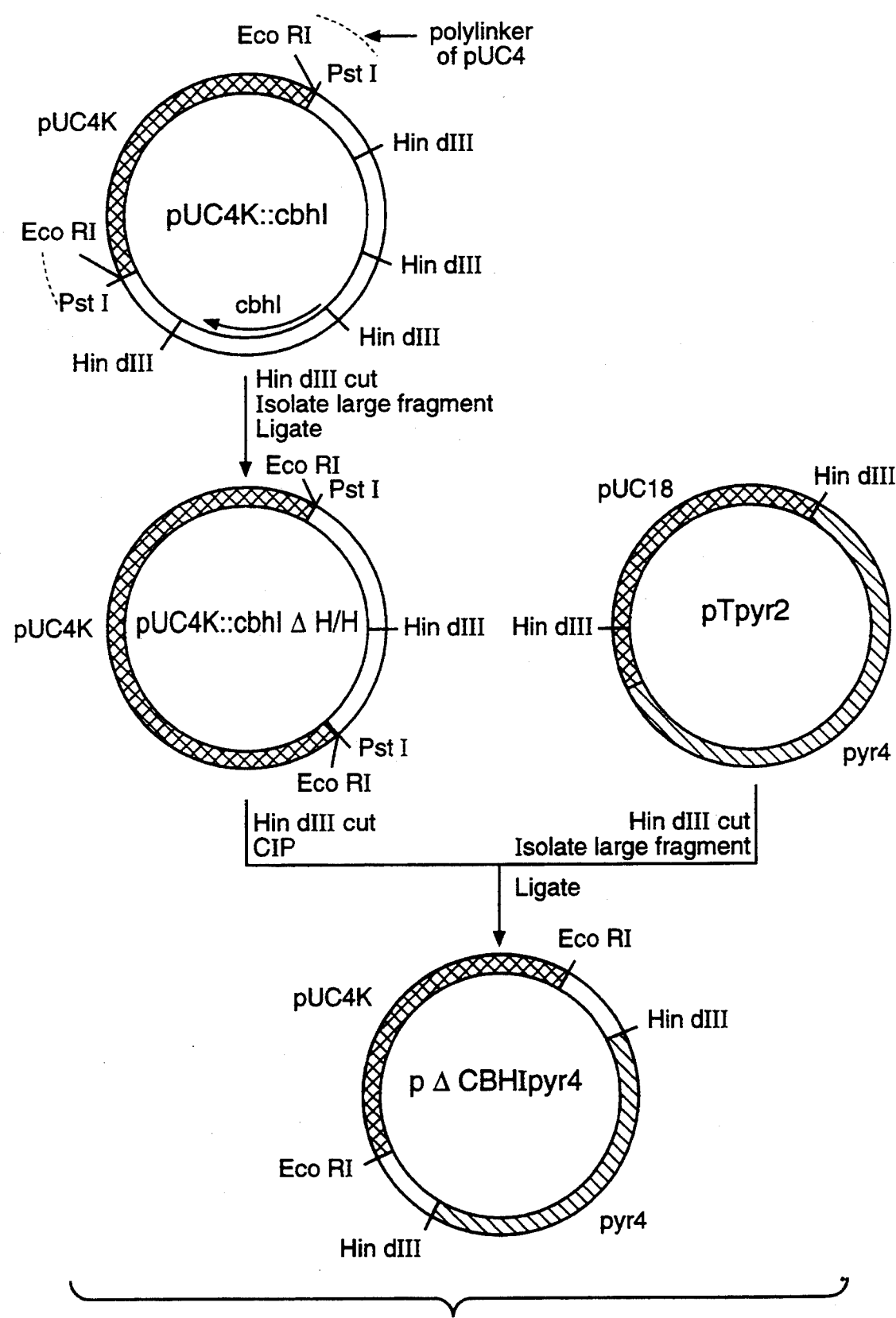
FIG._5

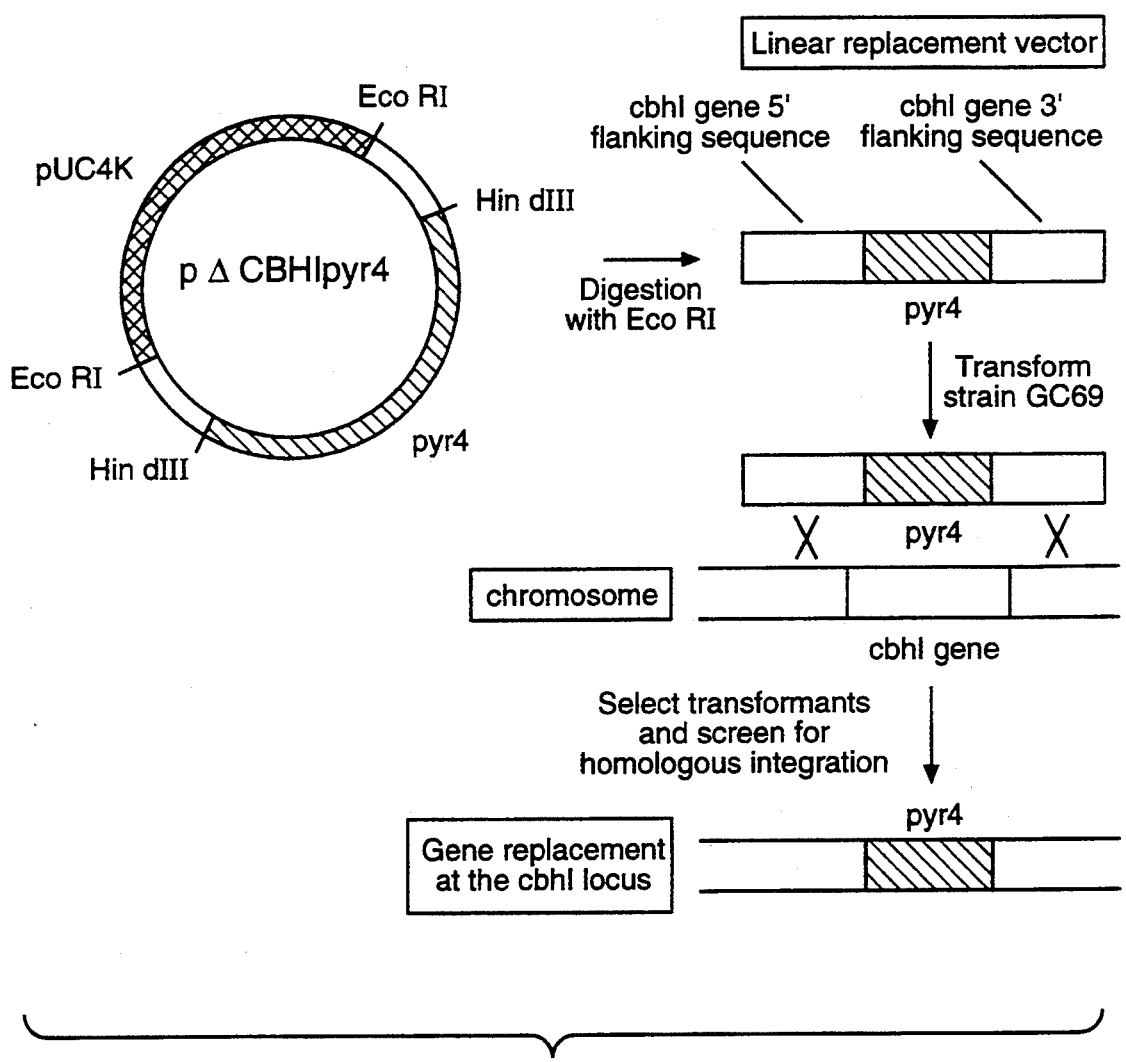
FIG._6

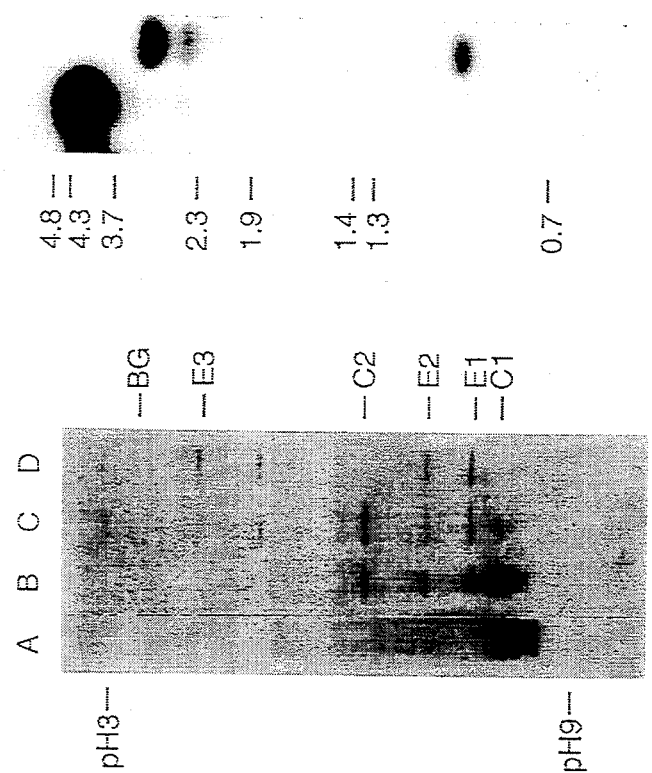
FIG._11
FIG._9
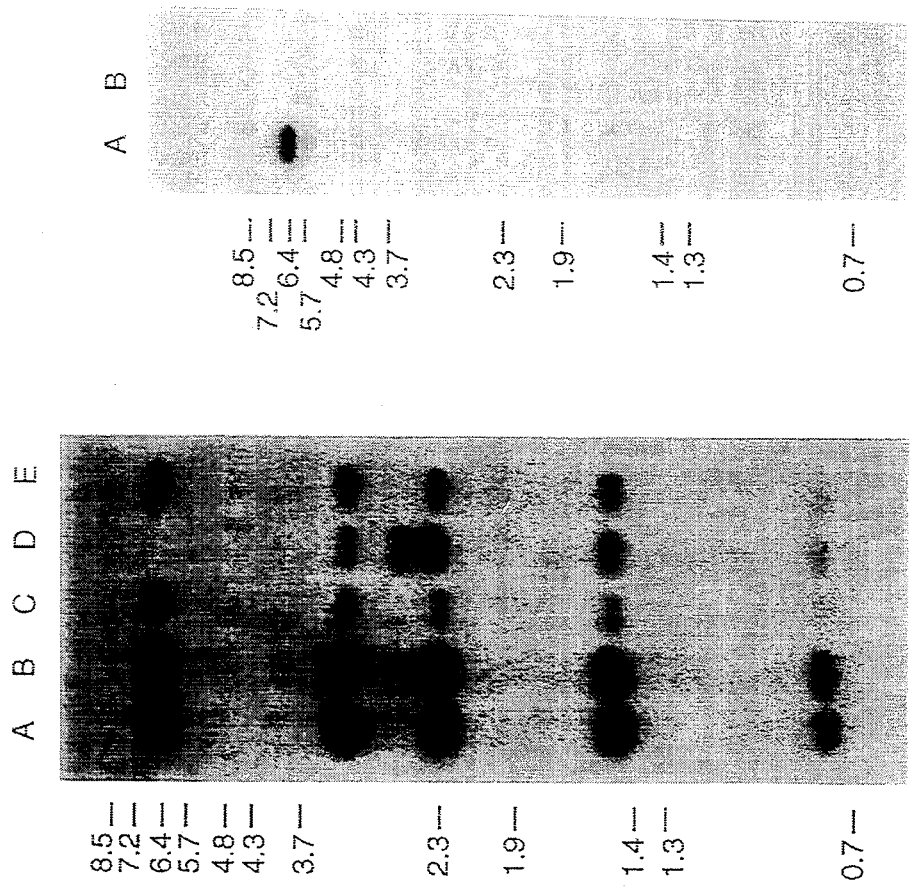
FIG._8
FIG._7

FIG._10A
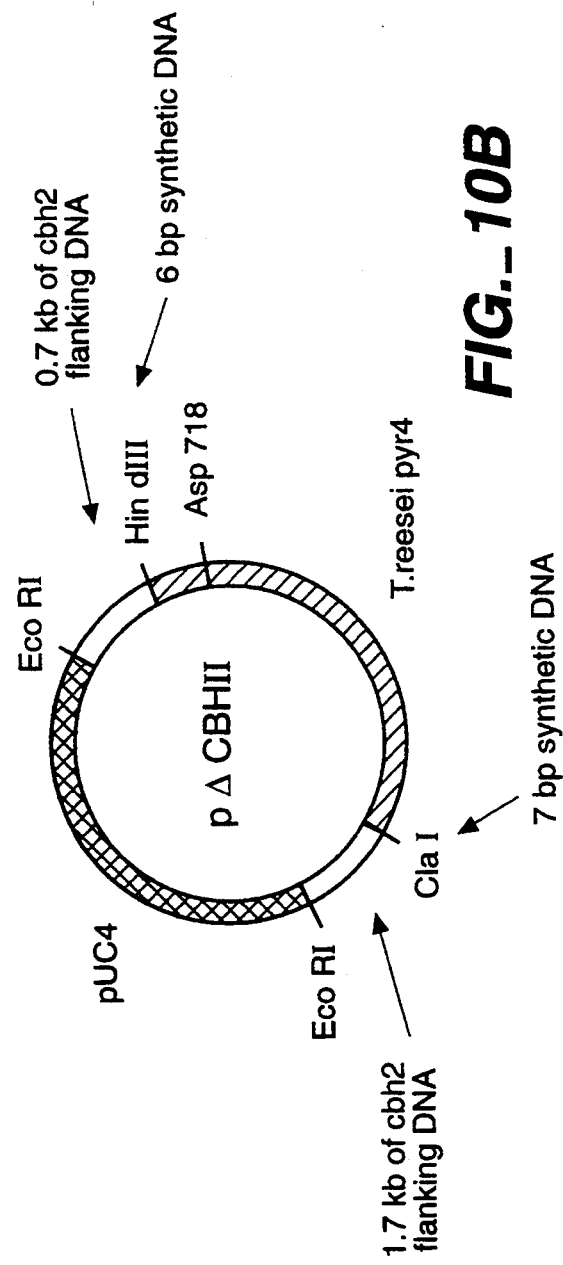
FIG._10B

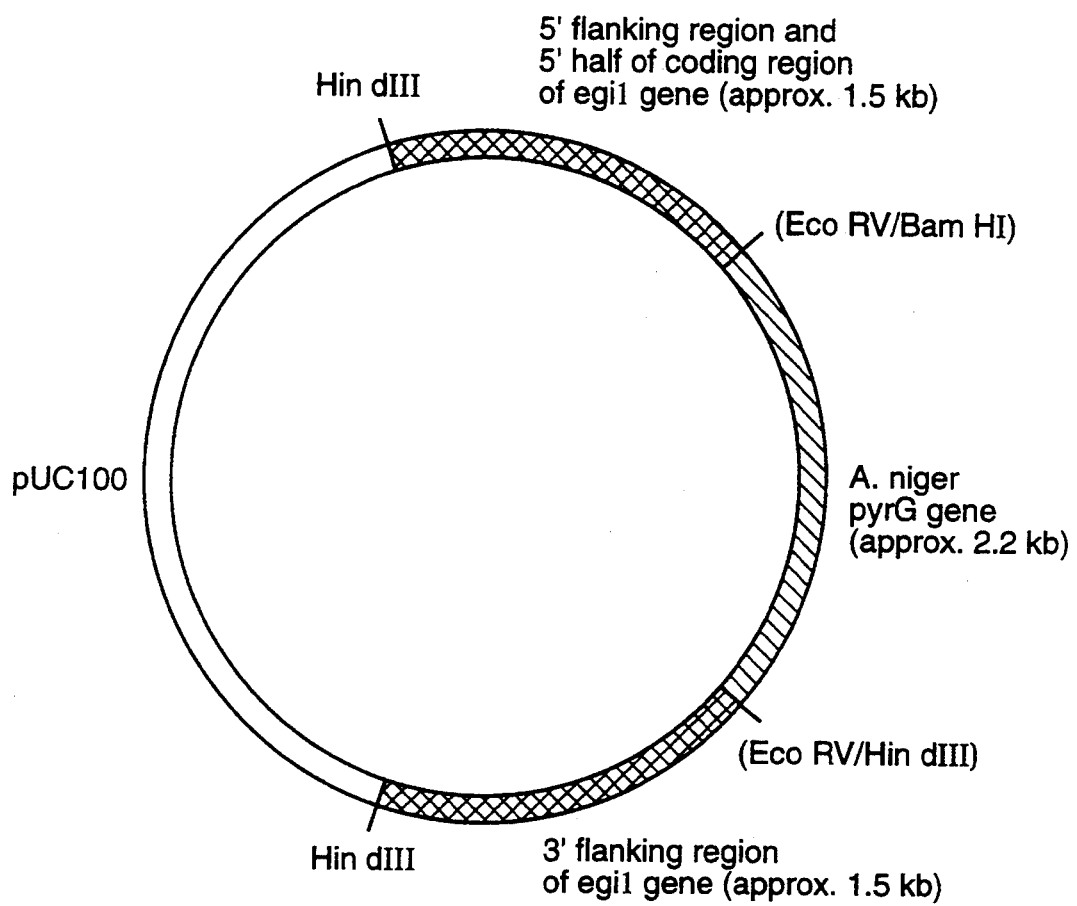
FIG._12

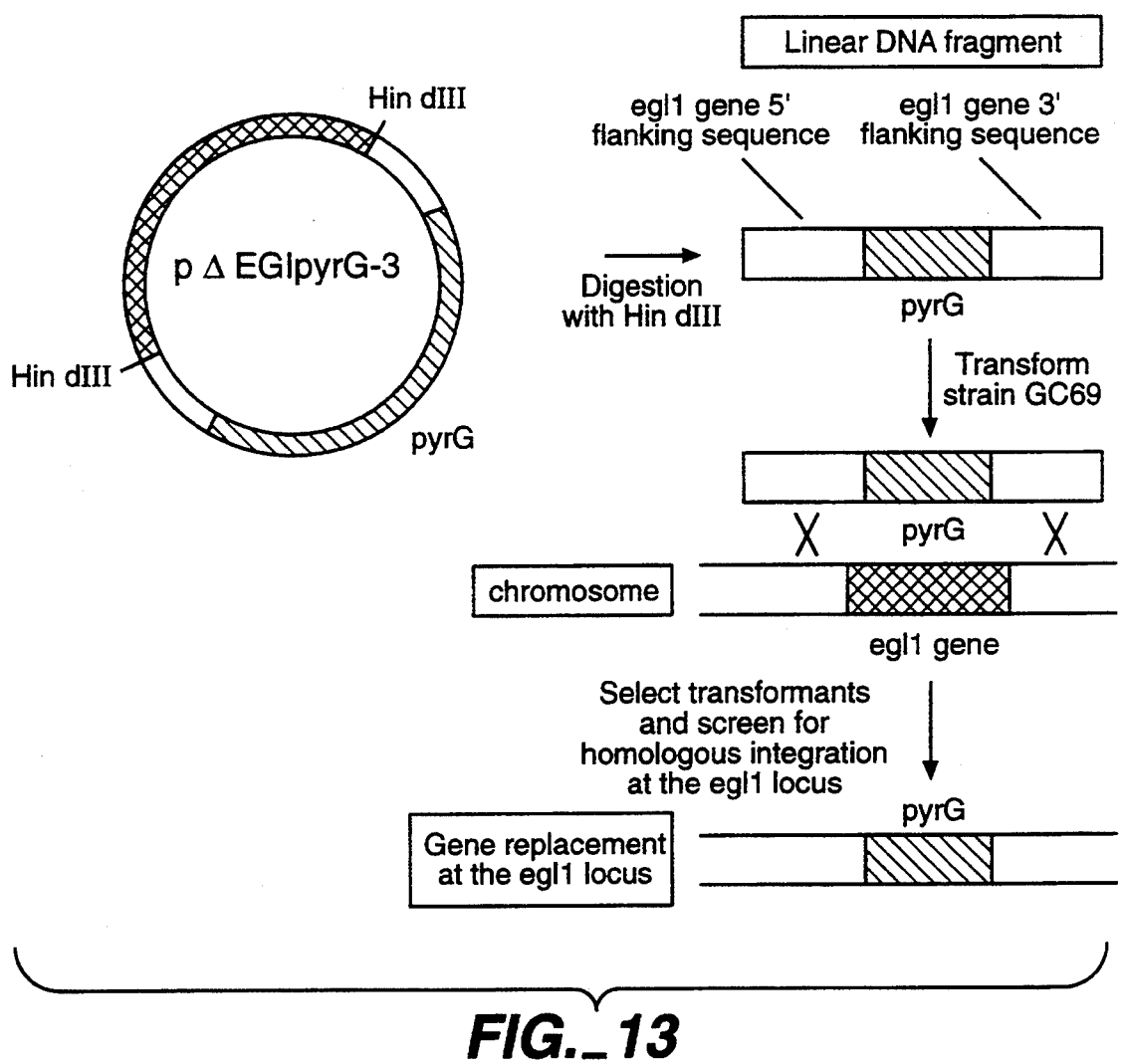
FIG._13

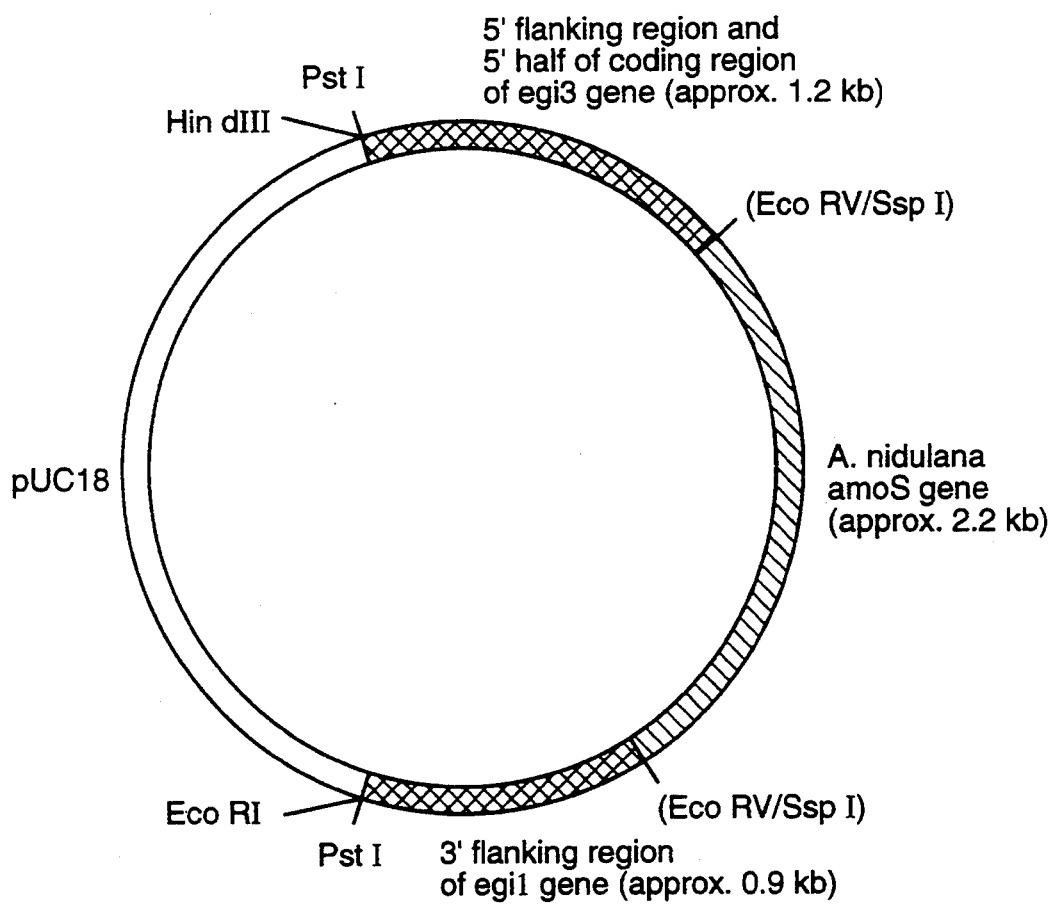
FIG._14

METHOD FOR PREPARING AN AQUEOUS SOLUTION ENRICHED IN BOTH EG-III & XYLANASE USING A LOW MOLECULAR WEIGHT ALCOHOL AND AN ORGANIC SALT

This is a continuation of application Ser. No. 07/862,641 filed on Apr. 3, 1992, now U.S. Pat. No. 5,320,960.

BACKGROUND OF THE INVENTION

1. Field of the Invention

The present invention is directed to methods for producing an aqueous solution containing a substantially pure EG III cellulase component. In particular, the methods of the present invention are directed, in part, to the removal of cellulase proteins, except the EG III cellulase component, from an aqueous mixture of cellulase proteins containing EG III by the addition of a low molecular weight alcohol to the aqueous mixture in the presence of an organic salt. In a preferred embodiment, the pH of the aqueous mixture is adjusted to at least about pH=7 before the addition of the alcohol. In another preferred embodiment, an inorganic salt is added to the EG III-rich supernate to precipitate the remaining contaminating proteins resulting in a substantially pure EG III composition. The methods of the present invention are also directed in part to the enrichment of xylanase from an aqueous solution containing xylanase.

2. State of the Art

Cellulases are known in the art as enzymes that hydrolyze cellulose ($\beta$-1,4-glucan linkages) thereby resulting in the formation of glucose, cellobiose, cellooligosaccharides, and the like. While cellulases are produced (expressed) in fungi, bacteria and the like, cellulase produced by certain fungi and, in particular by the fungus class Trichoderma spp. (especially *Trichoderma reesei*), have been given the most attention because a complete cellulase system capable of degrading crystalline forms of cellulose is readily produced in large quantities via fermentation procedures.

In regard to the above, Schulein, "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and $\beta$-glucosidases (EC 3.2.1.21) ("BG"). The fungal cellulase classifications of CBH, EG and BG can be further expanded to include multiple components within each classification. For example, multiple CBHs and EGs have been isolated from a variety of fungal sources.

The complete cellulase system comprising CBH, EG and BG components is required to efficiently convert crystalline cellulose to glucose. Isolated components are far less effective, if at all, in hydrolyzing crystalline cellulose. Moreover, a synergistic relationship is observed between the cellulase components particularly if they are of different classifications.

On the other hand, cellulases and components thereof, used either singularly or in combination, are also known in the art to be useful in detergent compositions. For example, endoglucanase components of fungal cellulases have been used for the purposes of enhancing the cleaning ability of detergent compositions, for use as a softening agent, and for use in improving the feel of cotton fabrics, and the like. However, there is a problem with using the EG I and EG II components derived from Trichoderma spp. and especially *Trichoderma reesei* in detergent compositions. Specifically, such components have their maximal activity at acidic pHs whereas most laundry detergent compositions are formulated for use at neutral or alkaline (pH>7 to about 10) conditions. While it is disclosed in U.S. Ser. No. 07/668,640 that the use of one or more acidic endoglucanase components of *Trichoderma reesei* in detergent compositions will provide improvements in softening, color retention/restoration and feel to cotton-containing fabrics even when treated under alkaline conditions, it is disclosed in U.S. Ser. No. 07/707,647 that the EG III component of Trichoderma spp. provides for superior and unexpected advantages in detergent compositions as compared to the EG I and EG II components of *Trichoderma reesei*.

Specifically, the EG III cellulase component has been found to possess significant enzymatic activity under alkaline conditions and is particularly suited for use in laundry conditions where a neutral or alkaline detergent wash medium is employed.

In addition to its use in laundry detergents, the substantially pure EG III cellulase component described herein can additionally be used in a pre-washing step in the appropriate solution at an intermediate pH where sufficient activity exists to provide desired improvements in color retention/restoration, softening and feel as disclosed in U.S. Ser. No. 07/707,647 filed May 30, 1991 and incorporated herein by reference.

Also, it is contemplated that the substantially pure EG III cellulase component described herein can be used in home use as a stand alone composition suitable for restoring color to faded fabrics (see, for example, U.S. Pat. No. 4,738,682, which is incorporated herein by reference in its entirety) as well as used in a spot-remover.

Additionally, it is further contemplated that the high activity under neutral to alkaline conditions of the EG III cellulase component would be beneficial in textile processes for treating cotton-containing fabrics (see U.S. Ser. Nos. 07/677,385 and 07/678,865 which are incorporated herein by reference in their entirety) as well as in silage and/or composting processes.

In contrast to the above, this invention is directed to efficient processes for the separation and purification of the EG III cellulase component from aqueous enzyme mixtures, particularly from a complete cellulase composition and particularly for commercial scale production of the EG III cellulase component.

SUMMARY OF THE INVENTION

Specifically, the present invention is directed to a method for producing an aqueous solution containing substantially pure EG III cellulase component from an aqueous mixture containing cellulase proteins including EG III cellulase component. Accordingly, in one of its method aspects, the present invention is directed to a method for selectively removing substantially all of the cellulase proteins, other than the EG III component, from the aqueous mixture containing cellulase proteins including EG III cellulase which method comprises the addition to the aqueous mixture of an effective amount of a low molecular weight alcohol in the presence of an organic salt under conditions wherein substantially all of the other cellulase proteins are precipitated from solution, and removing the precipitate. In a preferred embodiment, the pH of the aqueous mixture is adjusted to at least about pH=7 before the addition of alcohol.

In another preferred embodiment of this invention, an inorganic salt is added to the EG III-rich supernate and all remaining cellulase proteins, other than EG III, are precipitated.

The methods of the present invention are also directed in part, to the isolation of an aqueous solution containing substantially pure xylanase from Trichoderma spp.

The aqueous mixture can be a filtered whole cell extract or, more preferably, a whole cellulase composition from a wild-type Trichoderma spp. strain, a genetically modified Trichoderma spp. strain, or any other aqueous mixture, compatible with the methods of this invention and containing cellulase proteins including EG III.

BRIEF DESCRIPTION OF THE DRAWINGS

FIG. 1 illustrates the RBB-CMC activity profile over a pH range at 40° C. for an EG enriched fungal cellulase composition derived from a strain of Trichoderma reesei transformed so as to be incapable of expressing CBH I and CBH II; as well as the activity profile of an enriched EG III cellulase composition derived from Trichoderma reesei over a pH range at 40° C.

FIG. 2 is an isoelectric focusing gel which, in Lane 1 displays the proteins expressed by a wild type Trichoderma reesei, in Lane 2 displays the proteins expressed by a strain of Trichoderma reesei transformed so as to be incapable of expressing EG I and EG II components; and in Lane 3 displays the proteins found in substantially pure EG III cellulase. The right hand margin of this figure is marked so as to identify the bands attributable to CBH I, CBH II, EG I, EG II EG III and xylanase.

FIG. 3 is the amino acid sequence obtained from two fragments of EG III.

FIG. 4 is an SDS-PAGE gel which in Lane 11 displays the proteins expressed by a strain of Trichoderma reesei transformed so as to be incapable of expressing EG I and EG II components; in Lane 2 displays the proteins found in substantially pure EG III cellulase obtained by the method of Part A in Example I; and in Lane 12 displays pure EG III obtained by the method of Example 2.

FIG. 5 is an outline of the construction of pΔCBHIpyr4.

FIG. 6 illustrates deletion of the T. reesei gene by integration of the larger EcoRI fragment from pΔCBHIpyr4 at the cbh1 locus on one of the T. reesei chromosomes.

FIG. 7 is an autoradiograph of DNA from T. reesei strain GC69 transformed with EcoRI digested pΔCBHIpyr4 after Southern blot analysis using a $^{32}$P-labelled pΔCBHIpyr4 as the probe. The sizes of molecular weight markers are shown in kilobase pairs to the left of the Figure.

FIG. 8 is an autoradiograph of DNA from a T. reesei strain GC69 transformed with EcoRI digested pΔCBHIpyr4 using a $^{32}$P labelled pIntCBHI as the probe. The sizes of molecular weight markers are shown in kilobase pairs to the left of the Figure.

FIG. 9 is an isoelectric focusing gel displaying the proteins secreted by the wild type and by transformed strains of T. reesei. Specifically, in FIG. 5, Lane A of the isoelectric focusing gel employs partially purified CBHI from T. reesei; Lane B employs a wild type T. reesei: Lane C employs protein from a T. reesei strain with the cbh1 gene deleted; and Lane D employs protein from a T. reesei strain with the cbh1 and cbh2 genes deleted. In FIG. 9, the right hand side of the figure is marked to indicate the location of the single proteins found in one or more of the secreted proteins. Specifically, BG refers to the β-glucosidase E1 refers to endoglucanase I, E2 refers to endoglucanase II, E3 refers to endoglucanase III, C1 refers to exo-cellobiohydrolase I and C2 refers to exo-cellobiohydrolase II.

FIG. 10A is a representation of the T. reesei cbh2 locus, cloned as a 4.1 kb EcoRI fragment on genomic DNA and FIG. 10B is a representation of the cbh2gene deletion vector pPΔCBHII.

FIG. 11 is an autoradiograph of DNA from T. reesei strain P37PΔCBHIPyr26 transformed with EcoRI digested pPΔCBHII after Southern blot analysis using a $^{32}$P labelled pPΔCBHII as the probe. The sizes of molecular weight markers are shown in kilobase pairs to the left of the Figure.

FIG. 12 is an outline of the construction of pΔEGI-pyrG-3.

FIG. 13 illustrates deletion of the egl1 gene by integration of the HindIII fragment from pΔEGIpyrG-3 at the egl1 locus on one of the T. reesei chromosomes.

FIG. 14 is an outline of the construction of pAΔE-GII-1.

DETAILED DESCRIPTION OF THE INVENTION

As noted above, the present invention generally relates to methods for producing substantially pure EG III cellulase component whether in an aqueous solution or as a recovered protein.

However, prior to discussing this invention in further detail, the following terms will first be defined:

1. Definitions

As used herein, the following terms have the following meanings:

"EG III cellulase" refers to the endoglucanase component derived from Trichoderma spp. or any microorganism producing a protein equivalent to EG III produced by Trichoderma spp. characterized by a pH optimum of about 5.5 to 6.0, an isoelectric point (pI) of from about 7.2 to 8.0 and a molecular weight of about 23 to 28 Kdaltons. Preferably, EG III cellulase is derived from either Trichoderma reesei or from Trichoderma viride. EG III cellulase derived from Trichoderma reesei has a pH optimum of about 5.5 to 6.0, an isoelectric point (pI) of about 7.4 and a molecular weight of about 25 to 28 Kdaltons. EG III cellulase derived from Trichoderma viride has a pH optimum of about 5.5, an isoelectric point (pI) of about 7.7 and a molecular weight of about 23.5 Kdaltons. Additionally, it is contemplated that the amino acid sequence of the EG III cellulase may be altered. Alteration of the active sites on this enzyme may lead to a variety of different changes such as different pH optima, different temperature optima or altered affinities for the substrate.

Because of its high pI, the EG III component is found in a region of an isoelectric focusing gel where high pI xylanases and other high pI components expressed by Trichoderma spp. are generally found. In fact, it has been hypothesized that the band identified as EG III in FIG. 2 was a degradation product of either EG I or II. However, gel isoelectric focusing gels of EG I and EG II deleted cellulase (prepared in the manner of U.S. Ser. Nos. 07/770,049 and 07/668,640 and as described in Examples 18 and 19 hereinbelow) demonstrated that this band was not attributable to a degradation product of either EG I or II. (See also FIG. 2).

It is noted that EG II has been previously referred to by the nomenclature "EG III" by some authors but current nomenclature uses the term "EG II". In any event, the EG II protein is substantially different from the EG III protein in its molecular weight, pI, and pH optimum as evidenced by Table I of Example 2 presented below.

"Substantially pure EG III component" refers to a an aqueous solution or composition of cellulase proteins containing at least 50 weight percent, more preferably at least 70 weight percent and most preferably at least 90 weight percent of EG III cellulase component based on the total weight of the cellulase proteins in the composition.

"Substantially free of other cellulase proteins" refers to a composition in which at least 50 weight 10 percent, more preferably 60 weight percent and most preferably at least 90 weight percent of the cellulase proteins, other than EG III, have been removed from the original aqueous mixture of cellulase proteins.

"Enriched in xylanase" refers to an aqueous solution or composition containing an increase in xylanase concentration by the processes of this invention by at least a factor of 4, more preferably by at least a factor of 10.

"Cellulase proteins" refers to cellulase proteins which contain any and all exo-cellobiohydrolase (CBH) proteins, endoglucanase (EG) proteins and β-glucosidase (BG) proteins derived from fungal sources or microorganisms genetically modified so as to incorporate and express all or a part of the cellulase genes obtained from a fungal source.

Collectively, all of such proteins (i.e. CBH, EG and BG proteins) are referred to as "cellulase proteins". Certainly, cellulase proteins do not include other proteins expressed by Trichoderma spp. including xylanases, proteases, amylases, etc.

"Endoglucanase (EG) components" refer to the EG components of Trichoderma spp. including the EG I, EG II and/or EG III components of *Trichoderma reesei*. The endoglucanase components of Trichoderma spp. (e.g., the EG I, EG II, EG III components of *Trichoderma reesei*, and the like) either alone or in combination, impart improved feel, improved appearance, softening, color enhancement, and/or a stone washed appearance to cotton-containing fabrics (as compared to the fabric prior to treatment) when these components are incorporated into a textile treatment medium and the fabric is treated with this medium. In addition to the above, EG III possesses substantial activity at alkaline pHs where many detergent compositions are employed.

"Exo-cellobiohydrolase ("CBH") components" refer to the CBH components of Trichoderma spp. including the CBH I and CBH II components of *Trichoderma reesei*. When used in the absence of the EG components of Trichoderma spp, the CBH components of Trichoderma spp. alone do not impart significant color retention/restoration and improved feel to the so-treated cotton-containing fabrics. Additionally, when used in combination with such EG components, the CBH I component of *Trichoderma reesei* can impart enhanced strength loss and incremental cleaning benefits to cotton-containing fabrics.

"β-Glucosidase (BG) components" refer to those components of cellulase which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized on aryl substrates such as p-nitrophenol B-D-glucoside (PNPG) and thus are often called aryl-glucosidases. It should be noted that not all aryl-glucosidases are BG components, in that some do not hydrolyze cellobiose.

2. Methodology

The present invention is directed in part, to the discovery that an aqueous solution containing EG III, and substantially free of other cellulase proteins can be obtained from an aqueous enzyme mixture by the addition of a low molecular weight alcohol. Surprisingly, under these conditions, substantially all of the cellulase proteins, other than EG III precipitate from solution leaving the solution containing EG III substantially free of other cellulase proteins. It has also been found that, under these conditions, substantially all of the cellulase proteins, except EG III precipitate leaving a solution enriched in xylanase.

In one preferred method of carrying out the present invention, an aqueous mixture containing cellulase, was filtered to remove cell debris and other solids and produced a liquid filtrate containing a mixture of enzymes including cellulase proteins. More preferably, a cell free cellulase composition, such as CYTOLASE 123 (commercially available from Genencor International, Inc., South San Francisco, Calif.) is used. In another method, the aqueous mixture could be obtained from any aqueous source including aqueous mixtures already enriched for EG III. More particularly the resulting EG III solution described in concurrently filed application, U.S. Ser. No. 862,846, entitled METHODS FOR PRODUCING SUBSTANTIALLY PURE EG III USING POLYETHYLENE GLYCOL, which is incorporated herein in its entirety by reference.

After the filtrate is obtained from the filtration step, organic salts may be added to the filtrate before contacting the filtrate with the alcohol. Without being limited to any theory, it is believed that in some cases, the addition of an organic salt may enhance the retention of the EG III component in solution.

Prior to addition of the alcohol, the pH of the aqueous mixture is preferably adjusted to at least about pH=7, more preferably a pH of about 7 to about 12, and even more preferably a pH of about 7.5 to about 10.5, most preferably to a pH of about 9.5.

Upon addition of an effective amount of low molecular weight alcohol to the aqueous mixture, the enzymes other than the EG III component are precipitated out of solution and the EG III component is preferentially retained in solution. The low molecular weight alcohol is added to the aqueous mixture under conditions which result in the precipitation of cellulase proteins other than EG III with the retention of EG III in the aqueous solution. The specific time and temperature constraints employed in this step are not critical but depend on the degree of purity and the amount of recovery desired. For example, longer holding time will lead to higher degrees of purity as will lower temperatures. The specific combination of time and temperature employed is within the skill of the art. In a preferred embodiment, such conditions would include a temperature range from about 10° C. to 30°C., more preferably from about 15° C. to 25°C.

The low molecular weight alcohol is mixed with the aqueous mixture in a preferred embodiment for about 1 minute to 5 hours, more preferably from 1 minute to 1 hour. The aqueous solution is then centrifuged and filtered to remove the precipitated contaminating enzymes resulting in a first supernate. The amount of EG III comprises at least approximately 50% of the total cellulase protein in the first supernate as determined by the gel electrophoresis method of Example 7.

The EG III component can then be purified from the first supernate by a variety of methods. In a preferred embodiment, an equal volume of cold ethanol is then added to the first supernate and the precipitate containing EG III is collected by centrifugation. Alternatively, the EG III component can be purified by ionic exchange chromatography (e.g., by methods described in the examples hereinbelow). The EG III component is then resuspended in a suitable buffer. Suitable buffers may be 10 mM sodium acetate pH=4.5, 10 mM sodium citrate pH=4.0 or other compatible buffers known in the art (i.e., buffers which do not denature the EG III cellulase component).

In another preferred method of carrying out the process of the present invention, a compatible inorganic salt is added to the first supernate. The addition of a sufficient amount of a compatible inorganic salt to the first supernate results in the precipitation of substantially all cellulase proteins and xylanase remaining in solution, other than the EG III component. This mixture is then centrifuged and filtered to remove the precipitated contaminating proteins resulting in a second supernate. EG III comprises at least 80% of the total cellulase protein in the second supernate, as determined by gel electrophoresis. The EG III can be further purified from the second supernate by a variety of methods as disclosed above.

One of the essential features of the process however, is the use of a low molecular weight alcohol. The alcohol has been found to be uniquely active and selective for precipitating cellulase proteins other than the EG III component, from aqueous mixtures containing numerous other cellulase components. The term "low molecular weight alcohol" as used in this invention means a $C_1$ to $C_3$ alcohol [eg. ethanol, methanol, propanol and reagent alcohol (about 95% ethanol and about 5% methanol)] or a mixture of the same. An "effective amount of a low molecular weight alcohol" is that amount added to the aqueous mixture which is necessary to selectively precipitate a sufficient amount of the cellulase proteins, except the EG III component, from the aqueous mixture to provide a substantially pure EG III component once the precipitated proteins are removed. Preferably the amount of a low molecular weight alcohol added is from about 1.5 to about 2.5 parts (v/v) of alcohol per volume of aqueous mixture, more preferably the amount is 2.0 to about 2.4 parts (v/v), most preferably the amount is about 2.2 parts (v/v).

It has been found that the amount of alcohol added involves a trade off between recovery and purity. At 1.5 parts alcohol, there is a greater recovery of EG III component, but more contamination by other proteins. At 2.5 parts alcohol, the EG III component is contaminated with only xylanase, but the recovery is lower. The best separation and recovery has been found at 2.2 parts (v/v) of alcohol.

The low molecular weight alcohol has been found to be particularly useful in separating the EG III cellulase component from an aqueous mixture of cellulase proteins because the aqueous mixture contains a high percentage of other cellulase proteins relative to the percentage of EG III. For example, the normal distribution of cellulase components in the CYTOLASE 123 cellulase system is believed to be as follows:

| CBH I | 45–55 weight percent |
| CBH II | 13–15 weight percent |
| EG I | 11–13 weight percent |
| EG II | 8–10 weight percent |
| EG III | 1–4 weight percent |
| BG | 0.5–1 weight percent |

Useful quantities of EG III component are obtained by the method of this invention. The loss of recovery of EG III component by the method of this invention, as compared to other methods, is compensated for by the speed of recovery of the EG III component. The procedure does not require extensive fractionation steps for purification, although such steps can be followed for further purification if desired. Further, the cost of the starting material is negligible as compared to the high value of the purified EG III component.

The term "organic salt" as it is used in this application means an organic salt containing at least one carbon atom and preferably 1 to 7 carbon atoms which when used in conjunction with the low molecular weight alcohol facilitates the purification of EG III. Such organic salts include, by way of example, sodium acetate, zinc acetate, sodium formate and sodium benzoate and the like. The concentration of the organic salt in the aqueous mixture can be varied to provide the desired result. Preferably, the amount of organic salt used is less than about 30% (w/v) per original volume of aqueous mixture, more preferably the amount is between about 5% to 20% (w/v), most preferably the amount is 10% (w/v). It is possible that the addition of an organic salt to the aqueous mixture prior to the addition of the low molecular weight alcohol may not be necessary where organic salts, such as sodium benzoate, are already present in the aqueous mixture. However, without the addition of the organic salt, the amount of the EG III component recovered would be reduced.

The term "inorganic salt" means a compatible inorganic salt which when used in conjunction with a low molecular weight alcohol facilitates the purification of EG III without denaturing the enzyme. Suitable inorganic salts include salts having a sulfate or ammonium ion, more preferably, ammonium sulfate. An "effective amount of a inorganic salt" is that amount which when added to an aqueous mixture containing alcohol will result in the precipitation of proteins other than the EG III component from the solution to provide a substantially pure EG III component after removal of the precipitate. Preferably, the amount of a inorganic salt added is an amount which creates a saturated solution.

The EG III cellulase component can be purified from the first filtered supernate or the second filtered supernate by methods known in the art. For example, the addition of an equal volume of cold ethanol to the supernate causes the precipitation of the Eg III component. The precipitate is collected and resuspended in an appropriate buffer. Suitable buffers are known in the art, for example 10 mM sodium acetate pH 4.5 and 10 mM sodium citrate pH 4.0. Alternatively, the EG III component can be purified by ionic exchange chromatography methods known in the art.

In another embodiment, the inorganic salt may be added to the original aqueous mixture containing cellulase. The addition of a low molecular weight alcohol to this aqueous mixture will result in the precipitation of EG III enzymes, other than EG III. This mixture is then centrifuged and filtered to remove the precipitated contaminating enzymes. The EG III component can be purified from the supernate by a variety of methods as disclosed above.

In another preferred embodiment of carrying out the process of the present invention, the EG III component obtained from either of the three methods described above, removed from the supernate and resuspended in an appropriate buffer can be further purified by fractionation. The solution will be desalted using a Sephadex G-25 gel filtration resin column with 10 mM sodium phosphate buffer at pH 6.8. The desalted solution, would then be loaded onto a QA Trisacryl M anion exchange resin column. The fraction not bound on this column would contain EG III. This fraction will be desalted using a Sephadex G-25 gel filtration resin column equilibrated with 10 mM sodium citrate, pH 4.5. This solution will be again loaded onto a SP Trisacryl M cation exchange resin column and the EG III cellulase component eluted with an aqueous solution of 200 mM sodium chloride. The above process is described in concurrently filed application U.S. Ser. No. 862,846, entitled METHODS FOR PRODUCING SUBSTANTIALLY PURE EG III CELLULASE USING POLYETHYLENE GLYCOL, which is incorporated herein in its entirety.

In another preferred method of carrying out the process of the present invention, the EG III sample obtained from the cation exchange column can be further fractionated. The EG III sample will be desalted with a Sephadex G-25 column which had been previously equilibrated with 10 mM sodium citrate pH 4. The solution is then applied to a FPLC system using a Mono-S-HR 5/5 column (available from Pharmacia LKB Biotechnology, Piscataway, N.J.). The column will be eluted with 0–200 mM aqueous gradient of sodium chloride at a rate of 0.5 ml/minute.

It will be recognized that the above descriptions are preferred methods of carrying out the process of the present invention and that numerous variations of the above methods can be made in the process following the teachings of this invention. The various process conditions can be altered and reagents used can be changed to provide various desired or optimum operating conditions for recovery of the EG III cellulase component from any suitable aqueous mixture of enzymes containing the EG III component.

As will be recognized by those skilled in the art, the acids, bases and salts referred to above in the description of the process of this invention can be changed or substituted with equivalent acids, bases or salts which provide the desired pH or the desired salt content without interfering with the operation of the invention and which do not denature the EG III cellulase component.

EG III cellulase can be purified from any strain of Trichoderma spp. which produces EG III under suitable fermentation conditions or from any other microorganism producing cellulase proteins including EG III. While the particular source of EG III is not critical, preferred sources are *Trichoderma reesei* and *Trichoderma viride*. A particularly preferred source of EG III from *Trichoderma reesei* is CYTOLASE 123 cellulase which is commercially available from Genencor International, Inc., 180 Kimball Way, South San Francisco, Calif. 94080.

In order to enhance the efficiency of the isolation of EG III, it may be desirable to employ *Trichoderma reesei* genetically modified so as to overexpress EG III and/or to be incapable of producing one or more of EG I, EG II, CBH I and/or CBH II components or xylanase. This will necessarily lead to more efficient isolation of the EG III component by, for example, the alcohol extraction as described above. For example, substantially pure EG III prepared by fractionation methods set forth in the Examples below was employed to determine the amino acid sequence of parts of the protein using known sequencing methods (Example 4). This information can be used to prepare synthetic DNA probes in order to clone the gene encoding the EG III cellulase component. Once the EG III gene is cloned, it could be manipulated by recognized techniques and ultimately inserted into various Trichoderma spp. strains or into other microorganisms. See, for example, U.S. Ser. No. 07/770,049 filed Oct. 4, 1991, a continuation-in-part of U.S. Ser. No. 07/593,919, filed Oct. 5, 1990 and U.S. Ser. No. 07/668,640, filed Mar. 13, 1991, all of which disclose methods for genetically engineering *Trichoderma reesei* so that the modified microorganism is incapable of expressing one or more of the cellulase genes or xylanase genes and, in fact, may overproduce another cellulase gene. The disclosures of U.S. Ser. No. 07/770,049, filed Oct. 4, 1991, U.S. Ser. No. 07/593,919, filed Oct. 5, 1990 and U.S. Ser. No. 07/668,640, filed Mar. 13, 1991, are incorporated herein by reference in their entirety.

Using the methods described in these applications, *Trichoderma reesei* can be genetically manipulated so as to produce EG III with or without other cellulase proteins. Moreover, the methods described in those applications create *Trichoderma reesei* strains which do not produce any heterologous proteins.

Additionally, it would be possible to express the EG III-encoding gene in other microorganisms, including, but not limited to, yeast species such as *Sacchromyces cerevisiae, Pichia pastoris, Hansenula polymorpha, Kluyveromyces lactis, Yarrowia lipolytica, Schanniomyces occidentals*, etc. See, for example, PCT application Publication No. WO 85/04672. In order to obtain expression in these alternative, non-Trichoderma hosts, it may be necessary to functionally combine the EG III-coding DNA sequence with promoter and terminator sequences obtained from a gene from that particular host. It may also be necessary to substitute the DNA sequence encoding a secretion signal sequence from the alternative host for the DNA sequence encoding the EG III secretion signal sequence. Production and secretion of EG III in other organisms could enable EG III to be obtained in substantially pure form.

The substantially pure EG III cellulase described above can be further processed into a liquid diluent, granules, emulsions, gels, pastes, or the like. Such forms are well known to the skilled artisan. When a solid detergent composition is desired, the cellulase composition is preferably formulated as granules. Preferably, the granules can be formulated so as to contain a cellulase protecting agent. See, for instance, U.S. Ser. No. 07/642,669 filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granules can be formulated so as to contain materials to reduce the rate of dissolution of the granule into the wash medium. Such materials and granules are disclosed in U.S. Ser. No. 07/642,596 filed on Jan. 17, 1991 as Attorney Docket No. GCS-171-US1 and entitled "GRANULAR COMPOSITIONS" which application is incorporated herein by reference in its entirety.

The following examples are offered to illustrate the present invention and should not be construed in any way as limiting the scope of this invention.

EXAMPLES

Example 1

Large Scale Purification of EG III From Cytolase 123 cellulase

A. Organic Salt and Low Molecular Weight Alcohol

To a cell free cellulase filtrate, CYTOLASE 123, (commercially available from Genencor International, Inc., South San Francisco, Calif., which is produced from wild type *Trichoderma reesei*), was added 10% sodium acetate (w/v). The pH was adjusted to 9.5 by the addition of 50% NaOH. After the acetate was dissolved, 2.2 parts (v/v) ethanol at room temperature were added with mixing to 1 part of the cellulase filtrate (volume based on the starting volume of the filtrate). The ethanol filtrate mixture was centrifuged at $10,000 \times$ g for 10 minutes and the primary supernate was collected and filtered. The primary supernate contains the EG III component. To this filtered supernate was added an equal volume of ethanol at $-15°$ C. This mixture was centrifuged at $10,000 \times$ g for 10 minutes and the precipitate collected. This precipitate was resuspended in buffer.

It has been determined by RBB-CMC activity by the method as described in Example 6 that approximately 21% to 100% of the total amount of EG III is recovered from the cellulase filtrate by this method. It was determined by gel electrophoresis, as described in Example 7, that the EG III component comprises at least approximately 50% of the total cellulase protein in the precipitate. The cellulase filtrate of this example further contains xylanase whose concentration has been enriched by this process (i.e., an increase in xylanase concentration by at least 4 fold) and another unknown contaminating protein.

The pH does not have to be adjusted after the addition of sodium acetate, but increasing the pH to about 9.5 improves the purification.

Other alcohols have been tried in place of ethanol. Methanol, propanol and reagent alcohol (95% ethanol and 5% methanol) give very similar effects. Reagent alcohol is as useful as pure ethanol and is less expensive.

Other salts have been tried in place of sodium acetate: zinc acetate, sodium formate and sodium benzoate. The zinc acetate appears to be equally good as the sodium salt. The formate and benzoate gave slightly elevated, though still acceptable, levels of contaminating proteins.

B. Addition of an Inorganic Salt

In another experiment, sufficient ammonium sulfate to result in an excess of a saturated solution was added to the primary filtered supernate of the above method at room temperature and mixed for approximately 1 hour. This mixture was centrifuged at $10,000 \times$ g for 10 minutes and the resultant secondary supernate collected and filtered. The secondary supernate contains the EG III component. The precipitate contains enriched xylanase. An equal volume of ethanol at $-15°$ C. was added to this secondary supernate and mixed for approximately 5 minutes, and the precipitate was collected by centrifugation at $10,000 \times$ g for 10 minutes. The precipitate was resuspended in buffer. 15 The addition of the ammonium sulfate reduces the amount of EG III component recovered of the total EG III component present in the original cellulase filtrate but increases the level of purity of the Eg III component. The EG III component comprises at least 80% of the total cellulase protein in the precipitate, as determined by gel electrophoresis.

Likewise, EG III cellulase from other strains of Trichoderma spp. can be purified. For example, EG III cellulase derived from *Trichoderma viride* has been described by Voragen et al., Methods in Enzymology, 160:243-249. This reference describes the EG III cellulase as having a molecular weight of about 23.5 Kdaltons, a pH optimum of 5.5, and a pI of 7.7.

In order to enhance the efficiency of the isolation of EG III it may be desirable to employ *Trichoderma reesei* genetically modified so as to overexpress EG III and/or to be incapable of producing one or more EG I, EG II, CBHI and/or CBH II Components or xylanase components.

Example 2

Purification of EG III Via Fractionation

The substantially pure EG III component from the first supernate or second supernate obtained by in part a) of this example may be further purified by fractionation after precipitation and resuspension in an appropriate buffer. Additionally, the original cellulase filtrate can be purified by this method. Specifically, the fractionation is done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.).

In this example, CYTOLASE 123 cellulase, 0.5g, was desalted using a column of 3 liters of Sephadex G-25 gel filtration resin with 10 mM sodium phosphate buffer at pH 6.8. The desalted solution, was then loaded onto a column of 20 ml of QA Trisacryl M anion exchange resin equilibrated with 10 mM sodium phosphate buffer pH=6.8. The fraction bound on this column contained CBH I and EG I. The fraction not bound on this column contains CBH II, EG II and EG III. These fractions were desalted using a column of Sephadex G-25 gel filtration resin equilibrated with 10 mM sodium citrate, pH 4.5. This solution, 200 ml, was then loaded onto a column of 20 ml of SP Trisacryl M cation exchange resin. The EG III was eluted with 100 mL of an aqueous solution of 200 mM sodium chloride.

One particular method for further purifying EG III is by further fractionation of an EG III sample obtained in this Example 2. The further fraction was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in this Example 2 with a 20 ml Sephadex G-25 column which had been previously equilibrated with 10 mM sodium citrate pH 4. The solution was loaded onto the mono-S-HR 5/5 column previously equilibrated with 10 mM sodium citrate pH=4.0 and then eluted with 0-200 mM aqueous gradient of NaCl at a rate of 0.5 ml/minute with samples collected in 1 ml fractions. EG III was recovered in fractions 10 and 11 and was determined to be greater than 90% pure by gel electrophoresis. EG III of this purity is suitable for determining the N-terminal amino acid sequence by known techniques.

Substantially pure EG III has the following characteristics which are compared to the other endoglucanases isolated from Trichoderma reesei.

TABLE I

|  | MW | pI | pH optimum[1] |
|---|---|---|---|
| EG I | ~47-49 kD | 4.7 | ~5 |
| EG II | ~35 kD | 5.5 | ~5 |
| EG III | ~25-28 kD | 7.4 | ~5.5-6.0 |

1. pH optimum determined by RBB-CMC activity as per Example 3 below.

As can be seen from the above table, EG III has both a higher pH optimum and a higher pI as compared to the other endoglucanase components of Trichoderma reesei. In Example 3 below, it is seen that EG III also retains significant RBB-CMC activity under alkaline pHs.

Likewise, EG III cellulase from other strains of Trichoderma spp. can be purified. For example, EG III cellulase derived from Trichoderma viride has been described by Voragen et al., Methods in Enzymology, 160:243-249. This reference describes the EG III cellulase as having a molecular weight of about 23.5 Kdaltons, a pH optimum of 5.5, and a pI of 7.7.

In order to enhance the efficiency of the isolation of EG III it may be desirable to employ Trichoderma reesei genetically modified so as to overexpress EG III and/or to be incapable of producing one or more EG I, EG II, CBHI and/or CBH II components or xylanase components.

Example 3

Activity of Cellulase Compositions Over a pH Range

The following procedure was employed to determine the pH profiles of two different cellulase compositions. The first cellulase composition was a CBH I and II deleted cellulase composition prepared from Trichoderma reesei genetically modified in a manner similar to that described below so as to be unable to produce CBH I and CBH II components. Insofar as this cellulase composition does not contain CBH I and CBH II which generally comprise from about 58 to 70 percent of a cellulase composition derived from Trichoderma reesei, this cellulase composition is necessarily enriched in EG components. Since EG III is the most minor of the endoglucanase components of Trichoderma reesei, this composition predominates in EG I and EG II components.

The second cellulase composition was an approximately 20-40% pure fraction of EG III isolated from a cellulase composition derived from Trichoderma reesei via purification methods similar to Example 2. The activity of these cellulase compositions was determined at 40° C. and the determinations were made using the following procedures.

Add 5 to 20 µl of an appropriate enzyme solution at a concentration sufficient to provide the requisite amount of enzyme in the final solution. Add 250 µl of 2 weight percent RBB-CMC (Remazol Brilliant Blue R-Carboxymethyl-cellulose—commercially available from MegaZyme, 6 Altona Place, North Rocks, N.S.W. 2151, Australia) in 0.05M citrate/phosphate buffer at pH 4, 5, 5.5, 6, 6.5, 7, 7.5 and 8.

Vortex and incubate at 40° C. for 30 minutes. Chill in an ice bath for 5 to 10 minutes. Add 1000 µl of methyl cellosolve containing 0.3M sodium acetate and 0.02M zinc acetate. Vortex and let sit for 5-10 minutes. Centrifuge and pour supernatant into cuvettes.

Relative enzyme activity was determined by measuring the optical density (OD) of the solution in each cuvette at 590 nm. Higher levels of optical density correspond to higher levels of enzyme activity.

The results of this analysis are set forth in FIG. 1 which illustrates the relative activity of the CBH I and II deleted cellulase composition compared to the EG III cellulase composition. From this figure, it is seen that the cellulase composition deleted in CBH I and CBH II possesses optimum cellulolytic activity against RBB-CMC at near pH 5.5 and has some activity at alkaline pHs, i.e., at pHs from above 7 to 8. On the other hand, the cellulase composition enriched in EG III possesses optimum cellulolytic activity at about pH 5.5-6 and possesses significant activity at alkaline pHs.

Example 4

Isoelectric Focusing Gels

The purpose of this example is to illustrate isoelectric focusing gels of different EG III cellulase compositions. Specifically, cellulase produced by a wild type Trichoderma reesei; cellulase derived from a strain of Trichoderma reesei transformed so as to be incapable of expressing EG I and EG II cellulase proteins; and substantially pure EG III cellulase via purification methods similar to Example 2 were analyzed on isoelectric focusing gels.

Samples of these cellulases were analyzed by isoelectric focusing gels using a Pharmacia IEF system (FBE-3000, Pharmacia Inc., Piscataway, N.J.) and pH 3-10 precast gels (Servalyt Precote, available from Serva, Carl-Berg, Germany) according to the manufacturer's instructions. The gels were stained with Ephortec ™ stain (Serva Blue W, available from Serra Fine Biochemicals, Westbury, N.Y. 11590) to visualize the protein bands. The resulting gel is set forth in FIG. 2; wherein Lane 1 of FIG. 2 illustrates the isoelectric focusing gel of cellulase derived from a wild strain of Trichoderma reesei; Lane 2 illustrates the isoelectric focusing gel of cellulase derived from a strain of Trichoderma reesei so as to be incapable of expressing EG I and II; and Lane 3 illustrates the isoelectric focusing gel of substantially pure EG III cellulase obtained using the method of Example 2. In this figure, the margin adjacent to Lane I is marked to identify the bands corresponding to cellulase proteins so as to permit identification of the proteins.

This figure demonstrates that EG III is not a degradation product of either EG I or EG II proteins because, in Lane 2 of this figure, these proteins are not present while the EG III protein

Example 5

Peptide Sequencing of EG III

The substantially pure EG III component obtained by the purification method of Example 2, was precipitated by the addition of 0.9 ml of acetone to 0.1 ml of protein solution (at a concentration of 1 mg/ml) and incubation at −20° C. for 10 minutes. The protein was collected by centrifugation and the pellet dried and resuspended in 0.01 ml of 8M urea in 88% formic acid and 0.01 ml of cyanogen bromide (200 mg/ml) in 88% formic acid. The mixture was incubated at room temperature for four hours.

Individual peptides were purified on a HPLC (high pressure liquid chromatography) column. A Synchropak RP-4 column was equilibrated in deionized milliQ water with 0.05% TEA (triethylamine) and 0.05% TFA (trifluoroacetic acid). The sample was loaded onto the HPLC column and elution was carried out with 100% acetonitrile and 0.05% TEA and 0.05% TFA, with a gradient of 1% per minute. The amino-terminal regions of isolated peptides were sequenced by the method of Edman using a fully automated apparatus. The amino acid sequence obtained from two fragments of the EG III component are shown in FIG. 3

Example 6

Determination of Recovery of EG III Cellulase

20 μL of sample (or standard) was added to an individual eppendorf tube. Using an Eppendorf Repeat Pipette ™, 250 μl of substrate is added to samples and standards. All the eppendorf tubes were immediately vortexed. The tubes were then incubated in a 37° C. water bath for 30 minutes. At the end of incubation, 1 ml of precipitant was added to each tube using an Eppendorf Repeat Pipette. The tubes were vortexed vigorously. The samples were centrifuged for 3 minutes at 5,000×g. The supernate was poured into disposable cuvettes and the OD at 590 nm was determined using the OU/ml standard as blank.

The samples were diluted such that their activity fell within the standard range of 1.5 to 6.0 Units/mi. Samples were run in duplicate.

The standard was Genencor CYTOLASE 123 lot 87111. This is defined as containing 1000 RBB-CMC Units/ml. Appropriate dilutions were made to make standard solutions containing 0, 1.5, 3.0, 4.5 and 6.0 Units/ml. Standards were run in duplicate.

The substrate was prepared by adding 2 gms dry RBB-CMC (Azo-CM-Cellulose, obtained from Mega-Zyme, Ltd.) to 80 ml Just boiled deionized water. The mixture is stirred vigorously as it cooled to room temperature until all of the substrate had solubilized. 5.0 ml of a 2M sodium acetate solution was added. The pH of the solution was adjusted to 4.5 and the volume to 100 ml. A 1/100 dilution of a 2% solution of sodium azide was added to yield a final concentration of 200 ppm.

The precipitate was prepared by adding 33 grams anhydrous sodium acetate and. 4 grams zinc acetate to 150 ml distilled water. The pH of the solution was adjusted to 5.0 with 5M HCl and the volume was adjusted to 200 ml and 800 ml of ethanol was added.

The following results and estimates were obtained:

TABLE II

| SAMPLE | RBB-CMC UNITS ATTRIBUTABLE TO EG III | PERCENTAGE ESTIMATED |
| --- | --- | --- |
| aqueous mixture | 2025–10800 | 100% |
| first supernate from Example 1 | 2300 | 21–100% |

EG III is believed to have a specific activity of 15 to 20 RBB units per mg of protein.

Example 7

SDS-PAGE Gels of EG III Component

Samples to be run are diluted to contain approximately 1 to 3 mg of protein per ml. 100 μl of sample is placed in an eppendorf tube with 25 μl of 5X PDS, vortexed and heated at 98° C. for 5 minutes. Next, 12 μl of each sample is removed and loaded into a well. The gel is run at 40 mA with constant current for approximately 90 minutes in running buffer diluted to 1× strength with distilled water.

At completion the gel is removed from between the glass plates and immersed in a solution of Destain for 30 minutes with mild agitation to fix the protein. The gel is next stained with Coomasie Blue Stain with glacial acetic acid for 1 hour with mild agitation. The background stain is removed in Destain solution for approximately 18 hours.

Prepoured gels were obtained from Daiichi Pure Chemicals Co., Ltd. A gel with a gradient of 10 to 20% acrylamide or a non-gradient of 12.5% acrylamide was used. The electrophoresis was carried out in a Daiichi electrophoresis box.

5XPDS contains 2.5 ml of 20% sodium dodecylsulfate; 1 ml glycerol; 0.5 ml of 0.5M sodium phosphate pH 6.6; 1 ml distilled water; 0.1 ml beta-mercaptoethanol; and 10 mg bromophenol blue. The running buffer contains 30.25 g Tris base; 144.5 g ultra pure glycine; milli-Q $H_2O$ to 1 liter; 5 mls 20% SDS. The Destain contains 82.5 ml glacial acetic acid, 200 ml ethanol and $dH_2O$ to 1 liter. The Coomasie Blue Stain contains brilliant blue (Sigma No. B-0630) 2.5 g; ethanol 250 ml; $dH_2O$ to 1 liter. Before use mix 90 ml of coomasie blue stain with 10 ml glacial acetic acid.

The results are indicated in FIG. 4 which illustrates in Lane 11 the proteins expressed by a strain of *Trichoderma reesei* transformed so as to be incapable of expressing EG I and EG II components; and in lane 2 the proteins found in substantially pure EG III cellulase obtained by the method of Example 1 from a strain of *T. reesei* transformed so as to be incapable of expressing EG I and EG II components in which 10% w/v of zinc acetate and 2 parts ethanol were added to the cellulase mixture.

Example 8

Selection for Pyr4 Derivatives of *Trichoderma reesei*

The pyr4 gene encodes orotidine-5′-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 derivative strains using FOA. In practice, spores of *T. reesei* strain RL-P37 [Sheir-Neiss, G. and Montenecourt, B. S., *Appl. Microbiol. Biotechnol.* 20, p. 46–53 (1984)] were spread on the surface of a solidified medium containing 2 mg/ml uridine and 1.2 mg/ml FOA. Spontaneous FOA-resistant colonies appeared within three to four days and it was possible to subsequently identify those FOA-resistant derivatives which required uridine for growth. In order to identify those derivatives which specifically had a defective pyr4 gene, protoplasts were generated and transformed with a plasmid containing a wild-type pyr4 gene (see Examples 10 and 11). Following transformation, protoplasts were plated on medium lacking uridine. Subsequent growth of transformed colonies demonstrated complementation of a defective pyr4 gene by the plasmid-borne pyr4 gene. In this way, strain GC69 was identified as a pyr4 derivative of strain RL-P37.

Example 9

Preparation of CBHI Deletion Vector

A cbh1 gene encoding the CBHI protein was cloned from the genomic DNA of *T. reesei* strain RL-P37 by hybridization with an oligonucleotide probe designed on the basis of the published sequence for this gene using known probe synthesis methods (Shoemaker et al., 1983b). The cbh1 gene resides on a 6.5 kb PstI fragment and was inserted into PstI cut pUC4K (purchased from Pharmacia Inc., Piscataway, N.J.) replacing the Kan$^r$ gene of this vector using techniques known in the art, which techniques are set forth in Maniatis et al., (1989) and incorporated herein by reference. The resulting plasmid, pUC4K::cbh1 was then cut with HindIII and the larger fragment of about 6 kb was isolated and relegated to give pUC4K::cbh1ΔH/H (see FIG. 5). This procedure removes the entire cbh1 coding sequence and approximately 1.2 kb upstream and 1.5 kb downstream of flanking sequences. Approximately, 1 kb of flanking DNA from either end of the original PstI fragment remains.

The *T. reesei* pyr4 gene was cloned as a 6.5 kb HindIII fragment of genomic DNA in pUC18 to form pTpyr2 (Smith et al., 1991) following the methods of Maniatis et al., supra. The plasmid pUC4K::cbh1ΔH/H was cut with HindIII and the ends were dephosphorylated with calf intestinal alkaline phosphatase. This end dephosphorylated DNA was ligated with the 6.5 kb HindIII fragment containing the *T. reesei* pyr4 gene to give pΔCBHIpyr4. FIG. 5 illustrates the construction of this plasmid.

Example 10

Isolation of Protoplasts

Mycelium was obtained by inoculating 100 ml of YEG (0.5% yeast extract, 2% glucose) in a 500 ml flask with about $5 \times 10^7$ *T. reesei* GC69 spores (the pyr4 derivative strain). The flask was then incubated at 37° C. with shaking for about 16 hours. The mycelium was harvested by centrifugation at 2,750× g. The harvested mycelium was further washed in a 1.2M sorbitol solution and resuspended in 40 ml of a solution containing 5 mg/ml Novozym$^R$ 234 solution (which is the trade name for a multi-component enzyme system containing 1,3-alpha-glucanase, 1,3-beta-glucanase, laminarinase, xylanase, chitinase and protease from Novo Biolabs, Danbury, Conn.); 5 mg/ml MgSO$_4$. 7H$_2$O; 0.5 mg/ml bovine serum albumin; 1.2M sorbitol. The protoplasts were removed from the cellular debris by filtration through Miracloth (Calbiochem Corp, La Jolla, Calif.) and collected by centrifugation at 2,000 ×g. The protoplasts were washed three times in 1.2M sorbitol and once in 1.2M sorbitol, 50 mM CaCl$_2$, centrifuged and resuspended at a density of approximately $2 \times 10^8$ protoplasts per ml of 1.2M sorbitol, 50 mM CaCl$_2$.

Example 11

Transformation of Fungal Protoplasts with pΔCBHIpyr4

200 μl of the protoplast suspension prepared in Example 10 was added to 20 μl of EcoRI digested pΔCBHIpyr4 (prepared in Example 9) in TE buffer (10 mM Tris, pH 7.4; 1 mM EDTA) and 50 μl of a polyethylene glycol (PEG) solution containing 25% PEG 4000, 0.6M KCl and 50 mM CaCl$_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2M sorbitol and 50 mM CaCl$_2$ was added thereto and this solution was further mixed. The protoplast solution was then immediately added to molten aliquots of Vogel's Medium N (3 grams sodium citrate, 5 grams KH$_2$PO$_4$, 2 grams NH$_4$NO$_3$, 0.2 grams MgSO$_4$.7H$_2$O, 0.1 gram CaCl$_2$. 2H$_2$O, 5 μg α-biotin, 5 mg citric acid, 5 mg ZnSO$_4$. 7H$_2$O, 1 mg Fe(NH$_4$)$_2$. 6H$_2$O, 0.25 mg CuSO$_4$. 5H2O, 50 μg MnSO$_4$.4H2O per liter) containing an additional 1% glucose, 1.2M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene insert in pΔCBHIpyr4. These colonies were subsequently transferred and purified on a solid Vogel's medium N containing as an additive, 1% glucose and stable transformants were chosen for further analysis.

At this stage stable transformants were distinguished from unstable transformants by their faster growth rate and formation of circular colonies with a smooth, rather than ragged outline on solid culture medium lacking uridine. In some cases a further test of stability was made by growing the transformants on solid non-selective medium (i.e. containing uridine), harvesting spores from this medium and determining the percentage of these spores which will subsequently germinate and grow on selective medium lacking uridine.

Example 12

Analysis of the Transformants

DNA was isolated from the transformants obtained in Example 8 after they were grown in liquid Vogel's medium N containing 1% glucose. These transformant DNA samples were further cut with a PstI restriction enzyme and subjected to agarose gel electrophoresis. The gel was then blotted onto a Nytran membrane filter and hybridized with a $^{32}$P-labelled pΔCBHIpyr4 probe. The probe was selected to identify the native cbh1 gene as a 6.5 kb PstI fragment, the native pyr4 gene and any DNA sequences derived from the transforming DNA fragment.

The radioactive bands from the hybridization were visualized by autoradiography. The autoradiograph is seen in FIG. 7. Five samples were run as described above, hence samples A, B, C, D, and E. Lane E is the untransformed strain GC69 and was used as a control in the present analysis. Lanes A–D represent transformants obtained by the methods described above. The numbers on the side of the autoradiograph represent the sizes of molecular weight markers. As can be seen from this autoradiograph, lane D does not contain the 6.5 kb CBHI band, indicating that this gene has been totally deleted in the transformant by integration of the DNA fragment at the cbh1 gene. The cbh1 deleted strain is called P37PΔCBHI. FIG. 6 outlines the deletion of the T. reesei gene by integration through a double crossover event of the larger EcoRI fragment from pΔCBHIpyr4 at the cbh1 locus on one of the T. reesei chromosomes. The other transformants analyzed appear identical to the untransformed control strain.

Example 13

Analysis of the Transformants with pIntCBHI

The same procedure was used in this example as in Example 12, except that the probe used was changed to a $^{32}P$ labelled pIntCBHI probe. This probe is a pUC-type plasmid containing a 2 kb BglII fragment from the cbh1 locus within the region that was deleted in pUC4K::cbh1ΔH/H. Two samples were run in this example including a control, sample A, which is the untransformed strain GC69 and the transformant P37PΔCBHI, sample B. As can be seen in FIG. 8, sample A contained the cbh1 gene, as indicated by the band at 6.5 kb; however the transformant, sample B, does not contain this 6.5 kb band and therefore does not contain the cbh1 gene and does not contain any sequences derived from the pUC plasmid.

Example 14

Protein Secretion by strain P37PΔCBHI.

Spores from the produced P37PΔCBHI strain were inoculated into 50 ml of a Trichoderma basal medium containing 1% glucose, 0.14% $(NH_4)_2SO_4$, 0.2% $KH_2PO_4$, 0.03% $MgSO_4$, 0.03% urea, 0.75% bactotryptone, 0.05% Tween 80, 0.000016% $CuSO_4.5H_2O$, 0.001% $FeSO_4.7H_2O$, 0.000128% $ZnSO_4.7H_2O$, 0.0000054% $Na_2MoO_4.2H_2O$, 0.0000007% $MnCl.4H_2O$). The medium was incubated with shaking in a 250 ml flask at 37° C. for about 48 hours. The resulting mycelium was collected by filtering through Miracloth (Calbiochem Corp.) and washed two or three times with 17 mM potassium phosphate. The mycelium was finally suspended in 17 mM potassium phosphate with 1 mM sophorose and further incubated for 24 hours at 30° C. with shaking. The supernatant was then collected from these cultures and the mycelium was discarded. Samples of the culture supernatant were analyzed by isoelectric focusing using a Pharmacia Phastgel system and pH 3-9 precast gels according to the manufacturer's instructions. The gel was stained with silver stain to visualize the protein bands. The band corresponding to the cbh1 protein was absent from the sample derived from the strain P37PΔCBHI, as shown in FIG. 9. This isoelectric focusing gel shows various proteins in different supernatant cultures of T. reesei. Lane A is partially purified CBHI; Lane B is the supernatant from an untransformed T. reesei culture; Lane C is the supernatant from strain P37PΔCBHI produced according to the methods of the present invention. The position of various cellulase components are labelled CBHI, CBHII, EGI, EGII, and EGIII. Since CBHI constitutes 50% of the total extracellular protein, it is the major secreted protein and hence is the darkest band on the gel. This isoelectric focusing gel clearly shows depletion of the CBHI protein in the P37PΔCBHI strain.

Example 15

Preparation of pPΔCBHII

The cbh2 gene of T. reesei, encoding the CBHII protein, has been cloned as a 4.1 kb EcoRI fragment of genomic DNA which is shown diagrammatically in FIG. 10A (Chen et al., 1987, Biotechnology, 5:274–278). This 4.1 kb fragment was inserted between the EcoRI sites of pUC4XL. The latter plasmid is a pUC derivative (constructed by R. M. Berka, Genencor International Inc.) which contains a multiple cloning site with a symmetrical pattern of restriction endonuclease sites arranged in the order shown here: EcoRI, BamHI, SacI, SmaI, HindIII, XhoI, BglII, ClaI, BqlII, XhoI, HindIII, SmaI, SacI, BamHI, EcoRI. Using methods known in the art, a plasmid, pPΔCBHII (FIG. 10B), has been constructed in which a 1.7 kb central region of this gene between a HindIII site (at 74 bp 3' of the CBHII translation initiation site) and a ClaI site (at 265 bp 3' of the last codon of CBHII) has been removed and replaced by a 1.6 kb HindIII-ClaI DNA fragment containing the T. reesei pyr4 gene.

The T. reesei pyr4 gene was excised from pTpyr2 (see Example 9) on a 1.6 kb NheI-SphI fragment and inserted between the SphI and XbaI sites of pUC219 to create p219M (Smith et al., 1991, Curr. Genet 19 p. 27–33). The pyr4 gene was then removed as a HindIII-ClaI fragment having seven bp of DNA at one end and six bp of DNA at the other end derived from the pUC219 multiple cloning site and inserted into the HindIII and ClaI sites of the cbh2 gene to form the plasmid pPΔCBHII (see FIG. 10B).

Digestion of this plasmid with EcoRI will liberate a fragment having 0.7 kb of flanking DNA from the cbh2 locus at one end, 1.7 kb of flanking DNA from the cbh2 locus at the other end and the T. reesei pyr4 gene in the middle.

Example 16

Generation of a pyr4− Derivative of P37PΔCBHI

Spores of the transformant (P37PΔCBHI) which was deleted for the cbh1 gene were spread onto medium containing FOA. A pyr4− derivative of this transformant was subsequently obtained using the methods of Example 8. This pyr4− strain was designated P37PΔCBHIPyr−26.

Example 17

Deletion of the cbh2 Gene in a Strain Previously Deleted for cbh1

Protoplasts of strain P37PΔCBHIPyr−26 were generated and transformed with EcoRI digested pPΔCBHII according to the methods outlined in Examples 10 and 11.

Purified stable transformants were cultured in shaker flasks as in Example 14 and the protein in the culture supernatants was examined by isoelectric focusing, One transformant (designated P37PΔΔCBH67) was identified which did not produce any CBHII protein, Lane D of FIG. 9 shows the supernatant from a transformant deleted for both the cbh1 and cbh2 genes produced according to the methods of the present invention.

DNA was extracted from strain P37PΔΔCBH67, digested with EcoRI and Asp718, and subjected to agarose gel electrophoresis. The DNA from this gel was blotted to a membrane filter and hybridized with $^{32}$P-labelled pPΔCBHII (FIG. 11). Lane A of FIG. 11 shows the hybridization pattern observed for DNA from an untransformed *T. reesei* strain. The 4.1 kb EcoRI fragment containing the wild-type cbh2 gene was observed. Lane B shows the hybridization pattern observed for strain P37PΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA samples were also digested with EcoRI and Southern blot analysis was performed as above. In this Example, the probe was $^{32}$P labelled pIntCBHII. This plasmid contains a portion of the cbh2 gene coding sequence from within that segment of the cbh2 gene which was deleted in plasmid pPΔCBHII. No hybridization was seen with DNA from strain P37PΔΔCBH67 showing that the cbh2 gene was deleted and that no sequences derived from the pUC plasmid were present in this strain.

Example 18

Construction of pΔEGIpyr-3 and Transformation of a pyr4 Deficient Strain of *T. reesei*

The *T. reesei* egl1 gene, which encodes EGI has been cloned as a 4.2 kb HindIII fragment of genomic DNA from strain RL-P37 by hybridization with oligonucleotides synthesized according to the published sequence (Pentilla et al., 1986, *Gene* 45: 253–263; van Arsdell et al., 1987, *Bio/Technology*: 60–64).

This DNA fragment was inserted at the HindIII site of pUC100. An internal 1 kb EcoRV fragment which extended from a position close to the middle of the EGI coding sequence to a position beyond the 3' end of the coding sequence was removed by enzyme digestion and was replaced by ligation with a 2.2 kb BamHI-HindIII fragment containing the cloned *A. niger* pyrG gene (Wilson et al., 1988, *Nucl. Acids Res.* 16 p. 2339) to give pΔEGIpyrG-3 (FIG. 12). Transformation of a pyr4 deficient strain of *T. reesei* (strain GC69) by the method set forth in Examples 10 and 11, with pΔEGIpyr-3, after it had been digested with HindIII to release the fragment containing the pyrG gene with flanking regions from the egl1 locus at either end, led to transformants in which the genomic egl1 gene was disrupted by a mechanism outlined in FIG. 13. DNA was extracted from transformants, digested with HindIII, subjected to agarose gel electrophoresis and blotted onto a membrane filter. The filter was hybridized with radiolabelled pΔEGIpyr-3. In the untransformed strain of *T. reesei* the egl1 gene was present on a 4.2 kb HindIII fragment of DNA. However, following deletion of the egl1 gene by integration of the desired fragment from pΔEGIpyr-3 this 4.2 kb HindIII fragment disappeared and was replaced by a HindIII fragment approximately 1.2 kb larger in size. This pattern was observed for one transformant, which was designated ΔEGI-3.

Example 19

Construction of the PAΔEGII-1 and Deletion of the EGII Gene

The egl3 gene, encoding EG II (previously also known as EG III), was cloned from *T. reesei* strain RL-P37 as a 4 kb PstI genomic DNA fragment by hybridization with oligonucleotides synthesized according to the published sequence (Saloheimo et al., 1988, *Gene* 63:11–21). This DNA fragment was inserted into the PstI site of pUC18. This plasmid, pEGII, was subsequently digested with EcoRV to remove the entire EG II coding region on an approximately 2 kb segment extending from a position approximately 180 bp 5' of the EGII coding region to a position a few hundred base pairs beyond the end of the coding region. This segment was replaced with an SspI fragment of *Aspergillus nidulans* genomic DNA containing the amdS gene (Corrick et al., 1987, *Gene* 53:63–71) to create plasmid PAΔEGII-1 (See FIG. 14).

Wild-type strains of *T. reesei* are unable to grow on acetamide as a sole nitrogen source. Transformation with the amdS gene confers this ability and this is the basis for the selection system for transformants containing this gene.

Protoplasts of strain ΔEGI-3 were transformed, by the methods described in Examples 10 and 11, with pAΔEGII-1 which had been digested with HindIII and EcoRI and transformants able to grow on acetamide were selected. Subsequently, DNA was extracted from stable transformants, digested with pstI, subjected to agarose gel electrophoresis and blotted onto a membrane filter. The filter was hybridized with radiolabelled pAΔEGII-1. Homologous integration of the HindIII-EcoRI fragment from pAΔEGII-1, which contained egl3 flanking regions and amdS, at the genomic egl3 locus in a transformant lead to the 4 kb genomic PstI fragment containing the egl3 gene being replaced by smaller Pst1 fragments including two which would be approximately 1.0 and 2.8 kb in length. This pattern of hybridization was observed for one transformant which was designated strain ΔΔEG-1. This strain has deletions in both the EGI and EGII encoding genes and consequently is unable to produce either of these proteins.

The methods described in Examples 8–19 and in U.S. Ser. No. 07/770,049, filed Oct. 4, 1991, (incorporated herein by reference in its entirety) may be used to obtain *T. reesei* transformants which are unable to produce any or all of the following cellulase components; EG I, EG II, CBHI and CBHII, and the xylanase components. Additionally, the methods described may be used to obtain a *T. reesei* transformant which overexpresses the EG III cellulase component.

While the invention has been described in terms of various preferred embodiments, the skilled artisan will appreciate that various modifications, substitutions omissions and changes may be made without departing from the spirit and scope thereof. Accordingly, it is intended that the scope of the present invention be limited solely by the scope of the following claims, including equivalents thereof.

What is claimed is:

1. A method for preparing an aqueous solution containing both EG III and xylanase substantially free of other cellulase proteins from an aqueous mixture of cellulase proteins containing EG III, xylanase and other cellulase proteins which comprises:
(a) adding an amount of a low molecular weight alcohol selected from the group consisting of ethanol, methanol, propanol and mixtures thereof and an organic salt to said aqueous mixture containing cellulase proteins under conditions wherein substantially all of the cellulase proteins other than EG III and xylanase are precipitated out of the aqueous mixture and
(b) separating an aqueous supernate containing said EG III and xylanase from said aqueous mixture.

2. A method according to claim 1 further comprising adding the organic salt to the aqueous mixture before the addition of the alcohol.

3. A method according to claim 2 wherein the organic salt comprises a salt selected from the group consisting of sodium acetate, zinc acetate, sodium formate and sodium benzoate.

4. A method of claim 1 wherein the low molecular weight alcohol is ethanol.

5. A method of claim 1 wherein the beginning aqueous mixture is a filtered whole cell extract.

6. A method of claim 1 wherein the beginning aqueous mixture is a cell free cellulase mixture.

7. A method of claim 1, further comprising adjusting the pH of the aqueous mixture to a pH of at least about 7 before the addition of the alcohol.

8. A method of claim 7 wherein the pH of the aqueous mixture is adjusted to about 9.5.

* * * * *